(12) United States Patent
Alshurafa et al.

(10) Patent No.: US 11,222,422 B2
(45) Date of Patent: Jan. 11, 2022

(54) HYPERSPECTRAL IMAGING SENSOR

(71) Applicant: Northwestern University, Evanston, IL (US)

(72) Inventors: Nabil I. Alshurafa, Chicago, IL (US); Aggelos K. Katsaggelos, Evanston, IL (US); Oliver Strider Cossairt, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/492,214

(22) PCT Filed: Mar. 9, 2018

(86) PCT No.: PCT/US2018/021832
§ 371 (c)(1),
(2) Date: Sep. 9, 2019

(87) PCT Pub. No.: WO2018/165605
PCT Pub. Date: Sep. 13, 2018

(65) Prior Publication Data
US 2020/0005455 A1    Jan. 2, 2020

Related U.S. Application Data

(60) Provisional application No. 62/548,194, filed on Aug. 21, 2017, provisional application No. 62/469,352, filed on Mar. 9, 2017.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0075* (2013.01); *A61B 5/0077* (2013.01);
(Continued)

(58) Field of Classification Search
CPC combination set(s) only.
See application file for complete search history.

(56) References Cited

U.S. PATENT DOCUMENTS

2015/0228062 A1   8/2015   Joshi et al.
2015/0302160 A1   10/2015  Muthukumar et al.
(Continued)

OTHER PUBLICATIONS

O. Amft et al., "Detection of eating and drinking arm gestures using inertial body-worn sensors." In *Wearable Compniters, 2005. Proceedings. Ninth IEEE International Symposium on*, pp. 160-163, Oct. 2005.
(Continued)

*Primary Examiner* — Nam D Pham
(74) *Attorney, Agent, or Firm* — Bell & Manning, LLC

(57) ABSTRACT

Systems, methods, and computer readable media for hyperspectral imaging are provided. An example hyperspectral imaging sensor system to identify item composition includes an imager to capture hyperspectral imaging data of one or more items with respect to a target. The example includes a sensor to be positioned with respect to the target to trigger capture of the image data by the imager based on a characteristic of the target. The example includes a processor to prepare the captured imaging data for analysis to at least: identify the one or more items; determine composition of the one or more items; calculate an energy intake associated with the one or more items; and classify the target based on the energy intake.

20 Claims, 24 Drawing Sheets

(51) Int. Cl.
| | |
|---|---|
| A61B 5/11 | (2006.01) |
| G01N 21/27 | (2006.01) |
| G01N 33/02 | (2006.01) |
| G06K 9/00 | (2006.01) |
| G06K 9/62 | (2006.01) |
| H04N 5/33 | (2006.01) |
| H04N 7/18 | (2006.01) |

(52) U.S. Cl.
CPC .......... *A61B 5/1128* (2013.01); *A61B 5/4205* (2013.01); *A61B 5/4866* (2013.01); *A61B 5/7267* (2013.01); *G01N 21/27* (2013.01); *G01N 33/02* (2013.01); *G06K 9/00335* (2013.01); *G06K 9/6269* (2013.01); *G06K 9/6284* (2013.01); *H04N 5/332* (2013.01); *H04N 7/188* (2013.01); *A61B 2560/0223* (2013.01); *A61B 2562/0219* (2013.01); *A61B 2562/0233* (2013.01); *A61B 2562/0257* (2013.01); *A61B 2576/00* (2013.01); *G06T 2207/10024* (2013.01); *G06T 2207/10048* (2013.01); *G06T 2207/30004* (2013.01); *G06T 2207/30196* (2013.01)

(56) References Cited

U.S. PATENT DOCUMENTS

| | | |
|---|---|---|
| 2016/0034764 A1 | 2/2016 | Connor |
| 2016/0140870 A1* | 5/2016 | Connor ............... G01N 21/255 356/51 |
| 2016/0150213 A1 | 5/2016 | Mutti et al. |

OTHER PUBLICATIONS

O. Amft et al., "Bite weight prediction from acoustic recognition of chewing." *Biomedical Engineering, IEEE Transactions on*, 56(6): 1663-1672, 2009.
O. Amft et al., "Analysis of chewing sounds for dietary monitoring." In *UbiComp* '05, pp. 56-72, 2005.
O. Amft et al., "Methods for detection and classification of normal swallowing from muscle activation and sound." In *Pervasive Health Conference and Workshops*, 2006, pp. 1-10, Nov. 2006.
L. Arab et al., "Feasibility testing of an automated image-capture method to aid dietary recall." *European journal of clinical nutrition*, 65(10):1156-1162, 2011.
E. Barrett-Connor, "Nutrition epidemiology: how do we know what they ate?" *The American journal of clinical nutrition*, 54(1):182S-187S, 1991.
E. A. Carroll et al., "Food and Mood: Just-in-Time Support for Emotional Eating." In *Proceeding of IEEE Affective Computing and Intelligent Interaction (ACII)* '13, 2013.
E. K. Choe et al., "Understanding quantified-selfers' practices in collecting and exploring personal data." In *Proceedings of the 32nd annual ACM conference on Human factors in computing systems*, pp. 1143-1152. ACM, 2014.
F. Cordeiro et al., "Rethinking the mobile food journal: Exploring opportunities for lightweight photo-based capture." *CHI 2015*, 2015.
Y. Dong et al., "Detecting periods of eating during free-living by tracking wrist motion." *Biomedical and Health Informatics, IEEE Journal of*, 18(4):1253-1260, 2014.
D. H. Gustafson et al., "Explicating an evidence-based, theoretically informed, mobile technology-based system to improve outcomes for people in recovery for alcohol dependence." *Substance use & misuse*, 46(1):96-111, 2011.
M. Hall et al., The WEKA Data Mining Software: An Update. *SIGKDD Explorations*, 11(1), 2009.
M. A. Hall, "Correlation-based Feature Selection tor Machine Learning." *PhD Thesis*, Apr. 1999.

A. Kadomura et al., "Persuasive technology to improve eating behavior using a sensor-embedded fork." In *Proceedings of the 2014 ACM International Joint Conference on Pervasive and Ubiquitous Computing*, pp. 319-329. ACM, 2014.
H. Kalantarian et al., "A wearable nutrition monitoring system." In *Wearable and Implantable Body Sensor Networks (BSN), 2014 11th International Conference on*, pp. 75-80, Jun. 2014.
F. Kong et al., "Dietcam: Regular shape food recognition with a camera phone." In *Body Sensor Networks (BSN), 2011 International Conference on*, pp. 127-132. IEEE, 2011.
J. Liu et al., "An intelligent food-intake monitoring system using wearable sensors." In *Wearable and Implantable Body Sensor Networks (BSN), 2012 Ninth International Conference on*, pp. 154-160, May 2012.
J. Mankoff et al., "Using low-cost sensing to support nutritional awareness." In *UbiComp 2002: Ubiquitous Computing*, pp. 371-378. Springer, 2002.
D. C. Mohr et al., "The behavioral intervention technology model: an integrated conceptual and technological framework for ehealth and mhealth interventions." *Journal of medical Internet research*, 16(6), 2014.
I. Nahum-Shani et al., "Just-in-time adaptive interventions (jitais): An organizing framework for ongoing health behavior support." *Technical Report No.* 14-126, 2014.
C. Nederkoom et al. "Exposure to binge food in bulimia nervosa: finger pulse amplitude as a potential measure of urge to eat and predictor of food intake." *Appetite*, 42(2):125-130, 2004.
J. Noronha et al., "Platemate: crowdsourcing nutritional analysis from food photographs." In *UIST* '11, Oct. 2011.
L. Pina et al., "In situ cues for adhd parenting strategies using mobile technology." In *Proceedings of the 8th International Conference on Pervasive Computing Technologies for Healthcare*, pp. 17-24. ICST (Institute for Computer Sciences, Social-Informatics and Telecommunications Engineering), 2014.
J. P. Pollak et al., "Pam: a photographic affect meter for frequent, in situ measurement of affect." In *Proceedings of the SIGCHI conference on Human factors in computing systems*, pp. 725-734. ACM, 2011.
T. Rahman et al., "Bodybeat: A mobile system for sensing non-speech body sounds." In *Proceedings of the 12th Annual International Conference on Mobile Systems, Applications, and Services*, MobiSys '14, pp. 2-13, 2014.
S. Reddy, et al., "Image browsing, processing, and clustering for participatory sensing: Lessons from a dietsense prototype." In *Proceedings of the 4th Workshop on Embedded Networked Sensors, EmNets* '07, pp. 13-17, 2007.
E. Sazonov et al., Non-invasive monitoring of chewing and swallowing for objective quantification of ingestive behavior. *Physiological measurement*, 29(5):525, 2008.
M. Shuzo et al., "Discrimination of eating habits with a wearable bone conduction sound recorder system." In *IEEE Sensors* '09, pp. 1666-1669, 2009.
E. Stellar et al., "Chews and swallows and the microstructure of eating." *The American journal of clinical nutrition*, 42(5):973-982, 1985.
E. Thomaz et al., "A practical approach for recognizing eating moments with wrist-mounted inertial sensing." In *Proceedings of the 2015 ACM International Joint Conference on Pervasive and Ubiquitous Computing, UbiComp* '15, pp. 1029-1040, 2015.
E. Thomaz et al. "Feasibility of identifying eating moments from first-person images leveraging human computation." In *Proceedings of the 4th International SenseCam & Pervasive Imaging Conference*, pp. 26-33. ACM, 2013.
E. Thomaz et al., "Inferring meal eating activities in real world settings from ambient sounds: A feasibility study." In *Proceedings of the 20th International Conference on Intelligent User Interfaces*, pp. 427-431. ACM, 2015.
C. Vögele et al., "Psychophysiological responses to food exposure: an experimental study in binge eaters." *International Journal of Eating Disorders*, 21(2):147-157, 1997.
B. Wansink et al. The clean plate club: about 92% of self-served food is eaten. *International Journal of Obesity*, 39(2):371-374, 2015.

(56) References Cited

OTHER PUBLICATIONS

K. Witkiewitz et al., "Relapse prevention for alcohol and drug problems: that was zen, this is tao." *American Psychologist*, 59(4):224, 2004.

K. Yatani et al., "Bodyscope: A wearable acoustic sensor for activity recognition." *UbiComp* '12, pp. 341-350, 2012.

F. Zhu et al., An image analysis system for dietary assessment and evaluation. In *ICIP*, pp. 1853-1856, 2010.

The International Preliminary Report on Patentability issued in International Patent Application No. PCT/US2018/021832 dated Sep. 19, 2019, pp. 1-8.

\* cited by examiner

| RGB IMAGES | RICE (ACCURACY: 91.66%) | | | YAMS (ACCURACY: 65.83%) | | | STEW (ACCURACY: 54.44%) | | |
|---|---|---|---|---|---|---|---|---|---|
| CLASSIFIED AS | LOW FAT | MED FAT | HIGH FAT | LOW FAT | MED FAT | HIGH FAT | LOW FAT | MED FAT | HIGH FAT |
| LOW FAT | 60 | 0 | 0 | 33 | 7 | 0 | 43 | 2 | 15 |
| MED FAT | 14 | 45 | 1 | 17 | 19 | 4 | 31 | 20 | 9 |
| HIGH FAT | 0 | 0 | 60 | 6 | 7 | 27 | 25 | 13 | 22 |
| PRECISION | 0.81 | 1 | 0.98 | 0.59 | 0.58 | 0.87 | 0.43 | 0.57 | 0.47 |
| RECALL | 1 | 0.75 | 1 | 0.82 | 0.47 | 0.67 | 0.71 | 0.33 | 0.36 |

| HYPER-SPECTRAL IMAGES | RICE (ACCURACY: 99.44%) | | | YAMS (ACCURACY: 81.66%) | | | STEW (ACCURACY: 82.77%) | | |
|---|---|---|---|---|---|---|---|---|---|
| CLASSIFIED AS | LOW FAT | MED FAT | HIGH FAT | LOW FAT | MED FAT | HIGH FAT | LOW FAT | MED FAT | HIGH FAT |
| LOW FAT | 60 | 0 | 0 | 27 | 11 | 2 | 45 | 0 | 15 |
| MED FAT | 0 | 59 | 1 | 6 | 31 | 3 | 3 | 50 | 7 |
| HIGH FAT | 0 | 0 | 60 | 0 | 0 | 40 | 13 | 3 | 44 |
| PRECISION | 1 | 1 | 1 | 0.81 | 0.73 | 0.88 | 0.73 | 0.94 | 0.66 |
| RECALL | 1 | 0.93 | 1 | 0.67 | 0.77 | 1 | 0.75 | 0.83 | 0.73 |

FIG. 16

| True Labels | SVM Classified Labels | | | | |
|---|---|---|---|---|---|
| | Low Sugar | Medium Sugar | High Sugar | | |
| Low Sugar Banana | True Positive | False Negative | False Negative | | Sensitivity/Recall |
| Medium Sugar Banana | False Negative | True Positive | False Negative | | Sensitivity/Recall |
| High Sugar Banana | False Negative | False Negative | True Positive | | Sensitivity/Recall |
| | Precision | Precision | Precision | | Accuracy |
| | F1 Score | F1 Score | F1 Score | | |

FIG. 17

| True Labels | SVM Classified Labels (Hyperspectral) | | | |
|---|---|---|---|---|
| | Low Salt | Medium Salt | High Salt | |
| Low Salt Peas | 25 | 2 | 0 | 0.93 |
| Medium Salt Peas | 1 | 23 | 3 | 0.85 |
| High Salt Peas | 0 | 1 | 26 | 0.96 |
| | 0.96 | 0.88 | 0.90 | 0.91 |
| | 0.94 | 0.86 | 0.93 | |

FIG. 18A

| True Labels | SVM Classified Labels (RGB) | | | |
|---|---|---|---|---|
| | Low Salt | Medium Salt | High Salt | |
| Low Salt Peas | 12 | 9 | 6 | 0.44 |
| Medium Salt Peas | 13 | 6 | 8 | 0.22 |
| High Salt Peas | 2 | 5 | 20 | 0.74 |
| | 0.44 | 0.3 | 0.63 | 0.47 |
| | 0.44 | 0.25 | 0.68 | |

FIG. 18B

| Classification of Fat in Eggs (F-Measure) | | | |
|---|---|---|---|
| Fat Level | Low Fat | Medium Fat | High Fat |
| Hyperspectral | 0.95 | 0.88 | 0.90 |
| RGB | 0.32 | 0.38 | 0.38 |
| Fused | 0.94 | 0.91 | 0.89 |

FIG. 19

HYPERSPECTRAL IMAGING SENSOR

CROSS-REFERENCE TO RELATED APPLICATIONS

The present application claims priority benefit as a National Stage Application of International Application No. PCT/US18/21832, filed Mar. 9, 2018, which claims the priority benefit of U.S. Patent Application No. 62/548,194, filed Aug. 21, 2017 and U.S. Patent Application No. 62/469,352 filed Mar. 9, 2017, the contents of which are incorporated herein by reference in their entireties.

BACKGROUND

In the past few years, occurrence rates of metabolic disorders have skyrocketed. For example, cardiovascular heart disease is a leading cause of death around the world. While many aspects of these diseases are genetic, a significant portion of the risk can be mitigated through proper diet and exercise. However, maintaining a proper diet, for many people, is often difficult to sustain. Difficulty sustaining weight loss poses a challenge to both continuing a weight-loss trajectory and maintaining the weight lost. It is very difficult to determine the exact nutritional composition of a random food item unless all the ingredients are prepared from start to finish with meticulous attention to nutritional facts and portion sizes consumed. Additionally, gathering ingredient nutritional facts and portion sizes makes the assumption that individuals attempting to keep a healthy diet will be preparing all of their own meals. Even more complications are introduced when the individual chooses to eat outside of their homes or otherwise consume meals prepared by others. For at least these reasons, a technology is needed that provides accurate nutritional information of food consumed and integrates seamlessly into the user's life.

BRIEF DESCRIPTION OF THE DRAWINGS

FIG. 16 illustrates a table showing results of food calorie content identification using RGB and hyper-spectral image analysis.

FIG. 17 shows an example confusion matrix including labels classified using one or more SVMs.

FIG. 18A shows an example confusion matrix for hyperspectral image data and analysis.

FIG. 18B shows an example confusion matrix for RGB image data and analysis.

FIG. 19 shows an example of F-measures obtained for classification of fat in eggs using hyperspectral analysis alone, RGB analysis alone, and a fused hyperspectral/RGB analysis.

DETAILED DESCRIPTION OF CERTAIN EMBODIMENTS

Figure 1:
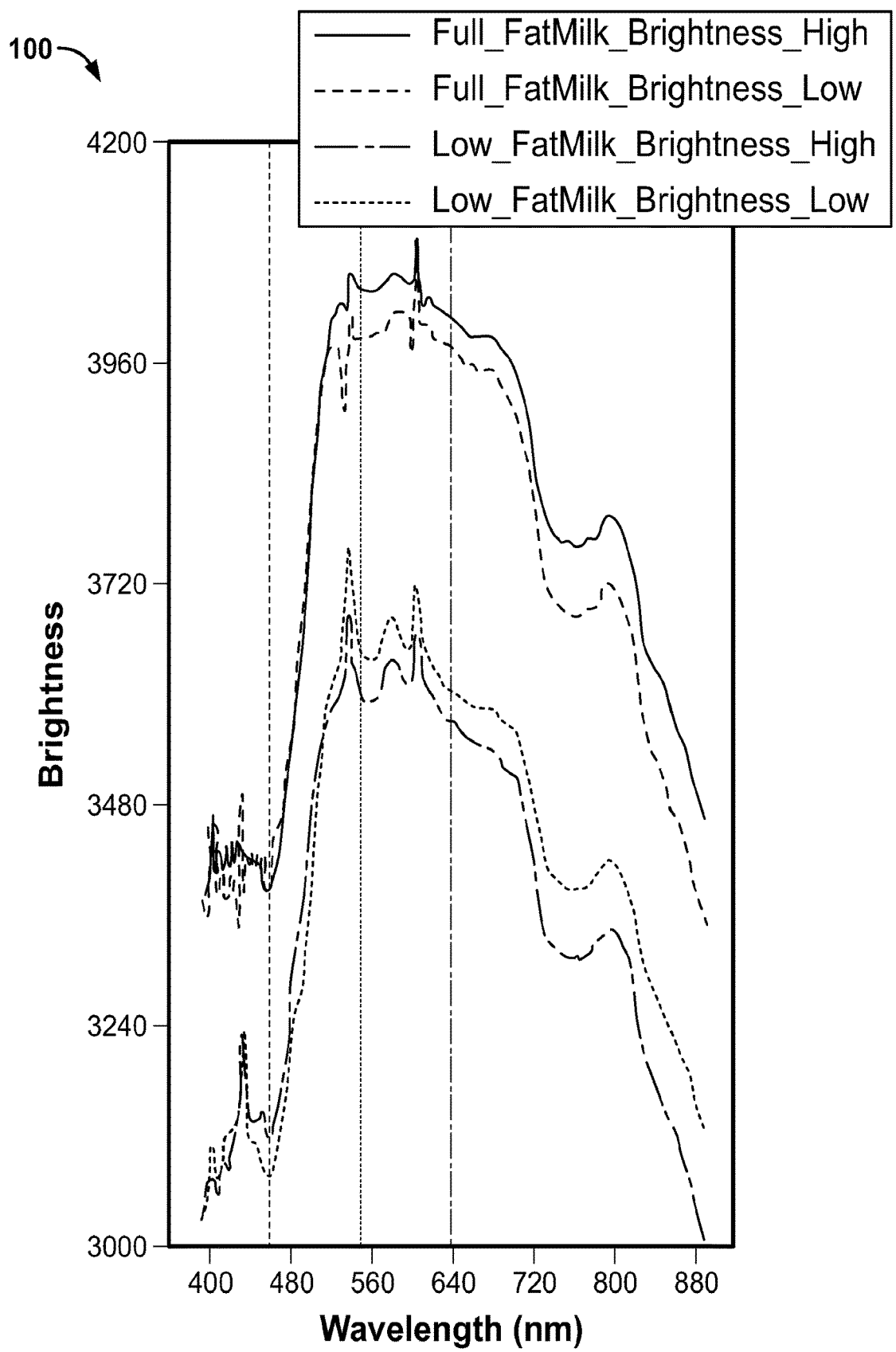
FIG. 1 illustrates four spectral signatures separating fat-free milk from full-fat milk.

The novel features of a device of this disclosure are set forth with particularity in the appended claims. A better understanding of the features and advantages of this disclosure will be obtained by reference to the following detailed description that sets forth illustrative examples, in which the principles of a device of this disclosure are utilized, and the accompanying drawings.

Overview

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

In recent years, there has been increase in obesity rates along with its adverse health effects stemming primarily from energy imbalance. As a result, rates of metabolic disorders such as cardiovascular heart disease have skyrocketed. Certain examples provide automated, intelligent wearable systems and associated methods of use that can aid individuals in more reliably monitoring their diet to prevent and fight off these disorders. Certain examples provide advanced cameras combined with optimized image processing algorithms and expanding food-image databases to form an automated diet monitoring system to estimate caloric and nutrient intake through automated food identification.

Certain examples provide image data analysis to evaluate food items. Red-Green-Blue (RGB)-color images can detect food items with reasonable accuracy, but RGB image analysis fails to distinguish between a large variability of food (e.g., ingredient) composition within a single food item. Instead, in certain examples, using hyperspectral imaging provides greater value (e.g., accuracy and precision, etc.) in differentiating within-food item variability. That is, hyperspectral imaging provides enhanced precision in evaluating nutritional composition compared to typical RGB-color images. A hyperspectral camera captures images of foods prepared and cooked with varying levels of fat, protein, carbohydrate, salt and sugar content. Given the large dimensionality of each hyperspectral image, a Principle Component Analysis (PCA) is applied to reduce the dimensionality of the data, and a Support Vector Machine (SVM) classifier with a Radial Basis Function (RBF) kernel is used to classify into sub-categories for each within-food item. Certain examples greatly enhance accuracy of distinguishing between ingredients or other food components compared to methods that only use RGB-color images. Certain examples using hyperspectral image analysis to better classify samples based on within-food caloric content.

Certain examples provide mobile hyperspectral imaging sensors to analyze object composition in conjunction with a passive sensor. For example, mobile health (mHealth) systems are provided to detect food items using a low-battery hyperspectral imaging sensor and passive sensing necklace, bracelet, etc., used to detect proximity, gesture, etc., to trigger the hyperspectral imaging sensor. Such portable hyperspectral imaging sensors can be used to target undernutrition in low-income countries and obesity and food allergies in the U.S. and other developed countries, for example. While examples are disclosed and described herein in the context of food items and associated composition and caloric information, a determination of composition can be facilitated for other items additionally or in the alternative.

Despite several efforts in the field of image recognition, conventional imaging technologies that only acquire morphology are not adequate for the accurate detection and assessment of characteristics or intrinsic properties of a product. Spectroscopic imaging covering the visible and near-IR spectrum (e.g., from 400 nm to 1100 nm) can help identify objects, such as food items, etc. Certain examples provide hyperspectral imaging fused with food database information to determine composition and caloric intake.

Hyperspectral imaging collects and processes information from across the electromagnetic spectrum. Hyperspectral imaging determines a spectrum associated with each pixel in an image being analyzed. The spectrum information can be processed for each pixel in the image to identify objects, component materials, and/or associated processes in the image, for example. While human eyes view images in terms of red, green, and blue (RGB), hyperspectral imaging divides light into many more frequency bands, in which spectral bands have fine wavelength resolution and cover a wide range of wavelengths. In hyperspectral imaging, contiguous spectral bands are measured. Different objects have different spectral "fingerprints" in the electromagnetic spectrum. Hyperspectral signals evaluate objects using a vast portion of the electromagnetic spectrum and identify those objects.

In hyperspectral imaging, sensors collect information as a set of images. Each hyperspectral image represents a certain narrow wavelength range of the electromagnetic spectrum (referred to as a spectral band). The set of images together forms a three-dimensional hyperspectral cube (x, y, λ), in which x and y represent two spatial dimensions of the captured image environment (e.g., the target eating, sleeping, moving, resting, etc.) and λ represents a spectral dimension defined by a range of wavelengths, for example. A detector array or camera can be used to capture a "snapshot" image of wavelength values for hyperspectral imaging analysis, for example.

Wearable and mobile smartphone technologies can be leveraged in systems and methods to assist individuals with monitoring, evaluating, and controlling their dietary intake. However, there are currently many limitations for mobile technology used for dietary assessment. These issues include that data acquired from phones usually include a large level of noise and variance, making acquired audio and/or image data difficult to accurately and precisely analyze. Furthermore, user involvement with these technologies can be burdensome and time consuming. Users often must take multiple pictures of their food and upload the images, which is a tedious and involved process. Another limitation of these technologies is that they are only capable of obtaining images in the visible light range (e.g., RGB). This makes it very difficult to distinguish caloric composition since two foods may visually appear similar but have drastically different nutritional values.

To remedy this problem, certain examples utilize hyperspectral imaging to provide a technological improvement in imaging analysis (and, in some examples, in place of or to augment audio analysis). Hyperspectral cameras obtain information from the near-infrared spectrum (e.g., 400 nm-1100 nm) and also from parts of the ultraviolet spectrum. As a result, hyperspectral cameras have the potential to differentiate between foods that appear similar visually but differ nutritionally and show promise for use in dietary management. Through feature extraction and classification of hyperspectral images of food, hyperspectral imaging can be used to distinguish food types and to classify foods of different nutritional value. Further, RGB image databases can be augmented with hyperspectral databases to improve accuracy in data analysis.

Short battery lifetime is a fundamental hurdle that limits the full potential of wearables to help gain a better understanding of people's habits. Certain examples utilize a proximity sensor as a passive sensing trigger to continuously monitor feeding gestures and trigger an associated system on and off. The system, once triggered, can capture hyperspectral image information for analysis, for example.

Additionally, sedentary individuals involve different dietary and health requirements that an individual who is active and working in manual labor all day. As a result, physical activity can be monitored such as using a tri-axial accelerometer.

Certain examples provide a hyperspectral imaging sensor that combines three main sensing units and associated processing capability: 1) a proximity sensor to capture feeding gestures and trigger a spectral imaging sensor; 2) a hyperspectral camera (e.g., with diffractive lens, sensor, and image signal processor (ISP)); and 3) a tri-axial accelerometer to determine physical activity and motion (e.g., to account for daily caloric intake/recommendation). The sensor device also includes a signal/control microprocessor, data storage, and communication interface (e.g., WiFi, Bluetooth, Bluetooth Low Energy (BLE), near field communication (NFC), etc.), for example.

To maintain battery life, the communication interface can be triggered when the neck-worn device is charging to transmit the data to a smartphone and/or other mobile computing device (e.g., smartphone, tablet computer, laptop, etc.) and then upload the data to a backend system (e.g., a laptop computer, a desktop computer, a server, etc.) for further processing and analysis. In some examples, depending on the operating environment, the communication interface can be modified to transmit data continuously to the mobile computing device.

Certain examples can be applied to understand and react to undernutrition, obesity, food allergies, etc. Certain examples more accurately and passively detect foods consumed and associated caloric intake without burdening the user through self-reporting.

For example, approximately one in every three children under the age of five is stunted, with many experiencing malnutrition rates well above the World Health Organization's emergency threshold. While several non-profit agencies are working to strengthen the resilience of rural populations, many areas do not receive assistance either because they do not meet the threshold for emergency aid, or aid is unable to adequately reach the region. Certain examples provide technology to help improve understanding of the undernutrition problem and help to build a sustainable strategy that will help solve the problem.

As another example, the American Medical Association now considers obesity a disease that increases the risk of other chronic diseases. Obesity is prevalent: more than a third of American adults (34.9%) are obese, and two-thirds are overweight or obese. Obesity is also a major driver of preventable healthcare costs, not only in the United States, but across the globe, including in developing countries. Frequent overeating—intake of excess kilocalories—fosters loss of energy balance, causing obesity. Because there currently exists no objective way to detect overeating in real time, or to predict overeating, there is no known behavioral intervention to prevent overeating by pre-empting it in the real time context of risk. Certain examples can help evaluate and address obesity.

As another example, more than 50 million Americans have some form of food allergy which affects 4 to 6% of children and 4% of adults (CDC). The following food items contribute to 90% of food allergies: eggs, milk, peanuts, tree nuts, fish, shellfish, wheat, and soy. Certain examples can detect these food items in an image and can help prevent allergic reactions.

As described above, existing technologies primarily use regular red-green-blue (RGB) images and geo-location (to limit the database of food options to select from) to identify food items (in hopes of detecting caloric content). However, RGB images are not sufficient to distinguish between different foods, and attempting to arrive at the composition of food. In contrast, certain examples can analyze images at varying spectra to help uniquely identify the food item in the image from captured hyperspectral imaging data.

Certain examples provide new technological solutions to measure food and nutrient intake at an individual and/or group level (e.g., in low income countries, etc.) and provide a set of diagnostic tools that can be used to assess nutrient status at the individual level, etc. Certain examples contribute to increasing the availability of valid, reliable and timely data to inform policy and programming at the country level, global level, individual level, etc.

Currently, there is no reliable automated method to identify foods consumed and their caloric content. Certain examples provide a determination for every food consumed of a unique food signature that is invariant to light (e.g., eating in the dark or light), heat (e.g., whether the food is consumed hot or cold), and slight variations in visual appearance (e.g., the beans consumed may look different with extra sauce).

Certain examples combine passive sensing, such as a long-lasting (e.g., reduced need to recharge) passive image capture necklace, with food composition tables including newly collected data of local foods and their caloric consumption to calculate caloric need to determine undernutrition. For example, a neck-worn hyperspectral video camera-based system includes a fish-eye lens that detects caloric intake triggered by feeding gestures from proximity sensors. To determine caloric need, a tri-axial accelerometer is incorporated to account for energy expenditure. The tri-axial accelerometer provides a single-point monitor for vibration/movement in three planes (e.g., x, y, z) to measure movement of a user and provide feedback to translate that movement into a measure of energy expenditure.

Certain examples provide algorithms to accurately detect feeding gestures, identify the existence of food in an image, implement image segmentation to separate food items, track hand movement (to associate food consumption with food item), and fuse existing databases with collected hyperspectral data to map food images to known foods in a food database (using deep neural networks) to determine caloric content. Certain examples provide methods to fuse spectral signatures to address mixed foods.

Certain examples provide a near real-time (e.g., by end of day) calculation of caloric need on a smartphone and/or other mobile computing device to test a behavioral intervention (e.g., a micro-randomized behavioral intervention, etc.) that detects undernutrition and inform new programs and/or advance existing programs.

Certain examples provide a highly scalable technology and methodology which can be mass-produced and deployed in remote settings. Certain examples can passively sense and map images to caloric content and determine whether someone is undernourished or not.

Description of Certain Example Motion Sensing, Image Capture, and Hyperspectral Image Analysis Despite several efforts in the field of image recognition, conventional imaging technologies that only acquire morphology are not adequate for the accurate detection and assessment of characteristics or intrinsic properties of a product. Spectroscopic imaging covering the visible and near-IR spectrum (e.g., from 400 nm to 1100 nm) can help identify unique spectral features that readily discriminate between food items. As an example, it is challenging to distinguish fat-free from full-fat milk using a traditional camera, but, as shown in the example of FIG. 1, a hyperspectral camera can provide a unique signature that helps distinguish the two types of milk (even in different lighting and heat conditions, after applying a normalization factor, for example). A graph 100 in FIG. 1 shows four (4) spectral signatures, in different lighting conditions, separating the fat-free milk from the full-fat milk. However, collecting data across the entire spectrum is not reasonable, and given existing food databases that use traditional RGB cameras, certain examples provide fusion-based systems and methods that combine databases to determine caloric intake. Thus, certain examples can use hyperspectral image data alone or in conjunction with RGB image data to determine food composition and associated caloric intake.

Figure 2:
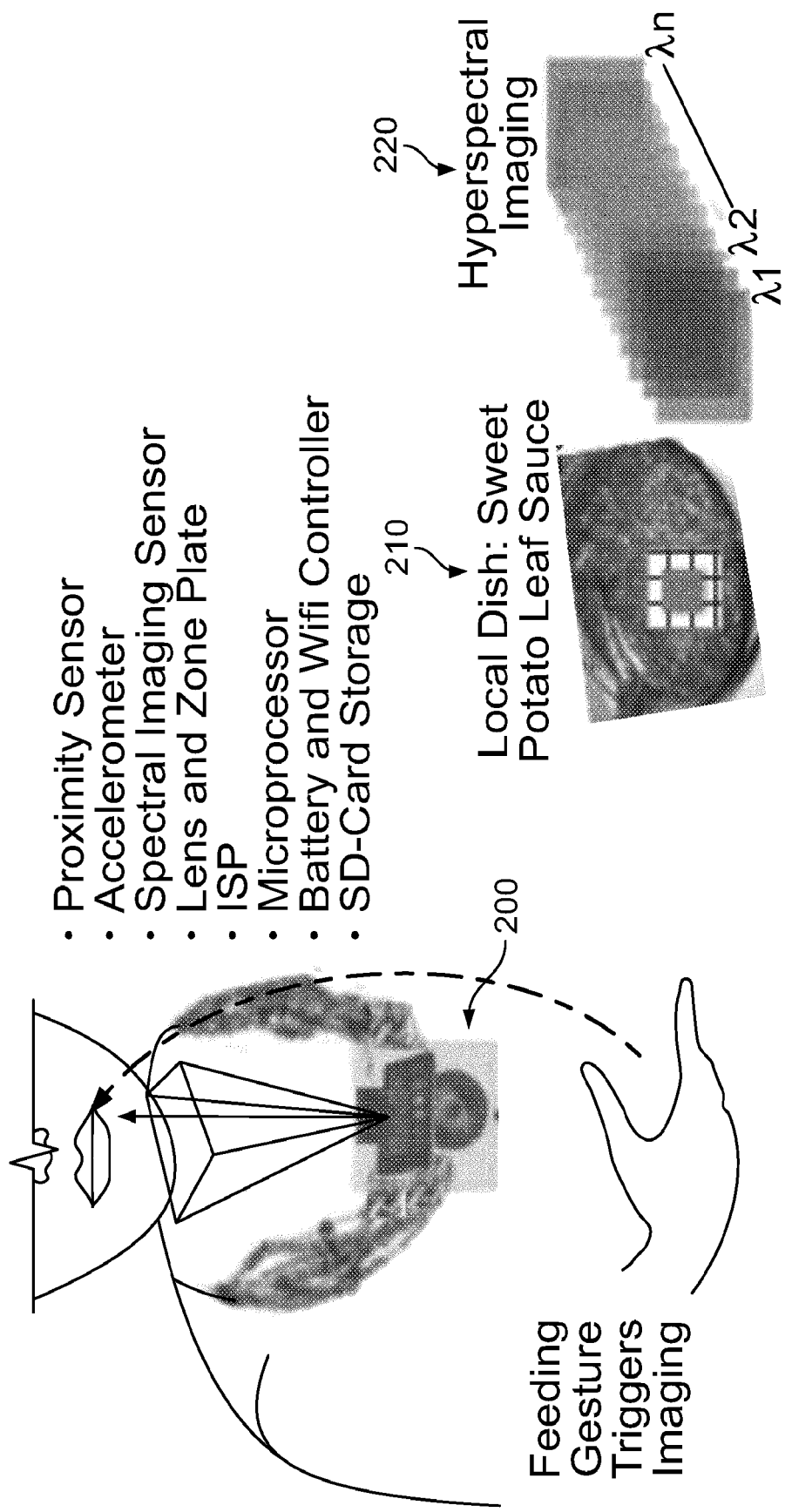
FIG. 2 illustrates an example hyperspectral imaging sensor system.

FIG. 2 illustrates an example hyperspectral imaging sensor system 200 including a proximity sensor, accelerometer, spectral imaging sensor, lens and zone plate, image signal processor (ISP), microprocessor, battery, communication interface, and data storage. The example system 200 can be triggered to analyze an object 210 to generate a hyperspectral image analysis 220, for example.

Certain examples use the hyper-spectral camera of the system 200 to record the morphological and spectral features of food items to empower machine learning algorithms to accurately identify the composition and nutrition content of the scanned food items. For example, the hyperspectral camera can include a wide-spectral imager covering visible and near-IR band from 400-1100 nm. Certain examples image in the near-infrared (IR) band as many of the meals are being consumed in very low-light conditions below 5 lux, where cameras operating in the visible light spectrum will produce very noisy data. The IR band, with an IR illuminator (automatically triggered when needed), can produce high-quality morphological and hyper-spectral data unobtrusively, for example. A convolutional neural network (CNN), recurrent neural network (RNN), and/or other machine learning construct can process the spectral frequency band information captured in the camera image(s) to correlate a spectral signature with an item (e.g., food, etc.) composition. Based on the composition, a calorie content can be determined, for example.

Certain examples provide hyper-spectral imaging including recording in video mode (e.g., collecting image data at a rate of three frames per second, etc.). For example, a hyper-spectral sensor can include expanded color filter arrays (CFA) rather than a RGB configuration in Bayer filters (e.g., with a 4×4 array of 16 bands of color filters manufactured by IMEC, etc.). This approach provides 10-15 nm spectral resolution but may be within a relatively narrow spectral band of only IR or visible light. The sensor is able to work with a wide range of optics in a very simple and robust package with reduced or minimal algorithm development, for example.

As another example, a hyper-spectral camera uses a combination of diffractive and achromatic lens to record a full 400-1100 nm spectrum using mobile camera sensors. The camera uses a highly chromatic Fresnel zone plate lens as an objective lens to focus different wavelengths to different focus depths, followed by a light-field camera to resolve depth differences and recover spectral information, for example. In certain examples, a zone plate encodes spectral information in longitudinal positions, and the light-field camera decodes the position information into spectral data. This approach provides similar spectral resolution as the above spectral sensor example, but images across the full spectral range, for example.

In hyperspectral imaging, light and dark reference images can be obtained to calibrate the system to its environment, which may include varying light intensity. The dark reference image can be used to eliminate dark current effects. The dark reference image can be acquired by placing a black cap over the camera, for example. The light reference image can be obtained by acquiring a white image such as a picture of a blank white sheet of paper. A corrected image can then be calculated as:

$$R = Ro - Rd / Rr - Rd \quad \text{(Eq. 1)},$$

where Ro is an acquired original hyperspectral image, Rr is the light reference image, Rd is the dark reference image.

The hyperspectral imaging system 200 provides data in the form of a datacube. The datacube stores a multi-dimensional array describing a time series of hyperspectral imaging data. Each dimension of the datacube represents a different measure, and each cell in the cube represents data related to the respective measure. By condensing the spectral information from two dimensions to one dimension, each image is represented as a three-dimensional array. The first two dimensions of the array represent the x and y spatial dimensions of the image. The size of these dimensions varies based on the size of the image taken. The third dimension is the spectral dimension, $\lambda$, and represents the intensity at a specific waveband. In certain examples, the spectral dimension has a size of 240 because the imaging system captures 240 wavebands of information. For example, an intensity of the third waveband at a particular pixel is the value located in the third index of this dimension.

Figure 3:
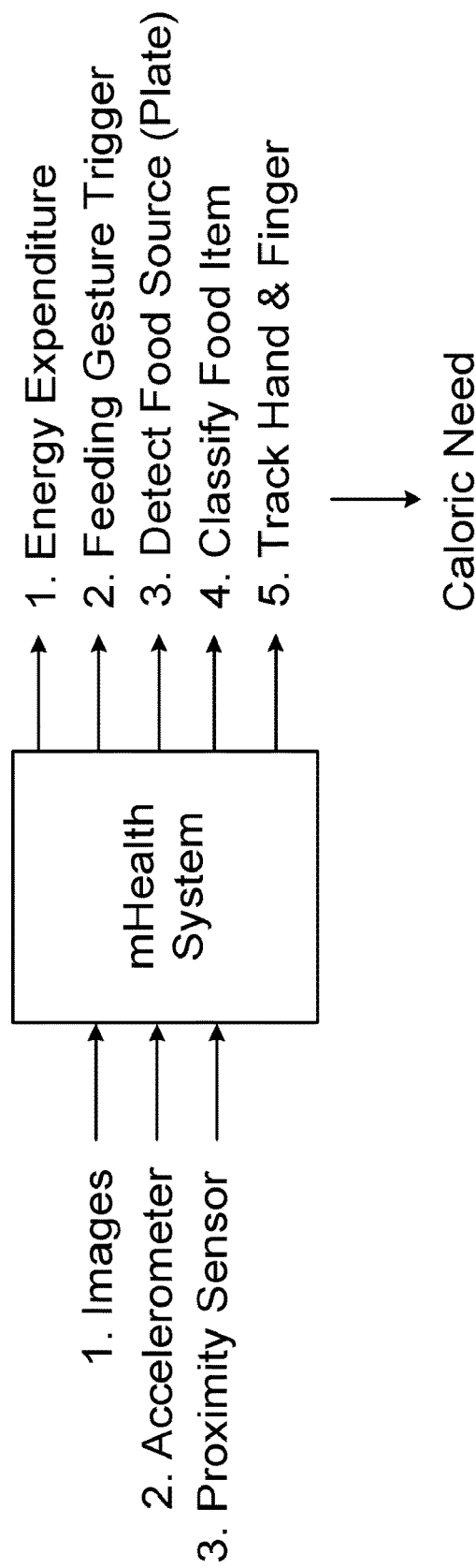
FIG. 3 illustrates an example mobile health system generating a caloric need.

Certain examples leverage acquired image information, accelerometer data, and proximity sensor information to detect foods and/or other items (e.g., separately and/or in combination) to recognize the item and its composition. For example, as shown in FIG. 3, the system 200 receives input images, accelerometer data, proximity sensor information, etc., and produces energy expenditure information, a feeding gesture trigger, a detected food source, a food item classification, hand/finger tracking, etc., to provide a caloric need/intake and/or other item composition information. For example, caloric expenditure can be generated from 3-axis inertial sensors, and an infrared proximity system can detect feeding gestures and trigger the hyperspectral camera after consecutive feeding gestures have been validated. Given consecutive images, food can be identified in a field of view and matched to a database, along with food item location, for example. Different food items can be segmented out in the field of view and classified at the source using information from an augmented food database, for example. Hand/finger tracking can be used to associate foods touched by hand with foods consumed (e.g., using information regarding a subject's average finger (e.g., thumb, index finger, etc.) and nail dimensions, etc.). Outputs can be combined to detect caloric need at a certain confidence interval, which can then be used to determine a condition such as whether the user is undernourished, overnourished, allergic, etc.

In certain examples, foods, activities, and/or other items can be detected and classified using deep neural networks (DNNs). For example, convolutional neural networks (CNNs), recursive neural networks (RNNs), and/or other deep learning networks can be used to detect and classify items and distinguish items over time. For example, Long Term Short Memory (LTSM) RNNs can properly distinguish between class labels using spatiotemporal data (e.g., video, etc.).

In certain examples, a mobile computing device, such as a smartphone, tablet, etc., executes an application that acts as an information gateway to transmit data from the device to a backend server (e.g., triggered when charging the device). The application can also provide communication and feedback to the user via the mobile device, for example.

In certain examples, a mobile hyperspectral camera system 200 can determine dietary intake, monitor food quality and environmental contamination, provide feedback to a user, etc. Certain examples work with and generate a food database that maps food items to individual caloric information, etc., based on information from the camera system 200.

In certain examples, before features can be extracted from captured image data, the image data is preprocessed. For example, preprocessing can include cleaning, dimension reduction, and path selection. For example, during the cleaning stage, the first 30 channels (e.g., 360 nm to 480 nm) of data are discarded and/or otherwise excluded as including a large amount of noise. To reduce the size of the data, the remaining 210 channels can be merged into seven larger bands by calculating the mean for every 30 bands. Then, twenty-four 30-pixel-by-30-pixel patches can be selected from each waveband to enhance the data set.

Features can be extracted from the preprocessed data set. For example, if fifteen different food dishes are present, with eleven dishes unique, some food items include multiple macromolecules (e.g., cookies include fat and sugar, etc.). When dishes appear visually different, features from the visible range of the spectra can be used to distinguish one dish from another. Features can include mean, standard deviation, maximum and minimum values, for example. The spectrum can include seven bands (e.g., including the visible range of the spectrum in the first three of the seven bands), resulting 3×4=12 total features in one example.

Macromolecule content detection can also be facilitated. First, obtained images are divided into training and testing datasets based on the lighting conditions of each image. Images taken in high and low intensity lighting conditions can be used as training data, for example, and images taken in medium intensity conditions can be used for testing the trained system (e.g., trained neural network such as a CNN, RNN, etc., a random forest, etc.). In certain examples, food items can have nearly identical visual appearances but differ in their molecular content (e.g., more salt content, less salt content, etc.). Thus, information from more than the visible range of the spectra is used to distinguish macromolecule content.

Prior to extracting features, the image data can be preprocessed. For example, each image can be cropped so that any part of the image not including food is removed. Further, the first 30 bands of data may be noisy and, therefore, removed. To reduce the large size of the dataset, a principal component analysis can be applied. Principal component analysis (PCA) is a statistical procedure that uses an orthogonal transformation to convert a set of observations of possibly correlated variables into a set of values of linearly uncorrelated variables called principal components. The number of principal components is less than or equal to the number of original variables.

The PCA can be used in hyperspectral imaging for dimension reduction and extracting features. The PCA functions by creating uncorrelated (orthogonal) components from correlated data. This allows for the use of only a few components to explain most of the variance within the data. Since only a few components need to be used, the PCA enables a much quicker analysis. For example, the first k principal components which incorporate 99% of the variance in the image data can be used.

After cleaning and reducing the data, training and testing data sets can be created based on lighting conditions. From these images, patches (e.g., 15×15×k, 30×30×k, etc.) can be extracted. A size of the patch can be dependent on an initial size of the image, for example. A mean spectrum of pixels in each patch can form a feature vector.

Classification methods can be applied to the data sets to distinguish different foods and their macromolecule content. Metrics used to evaluate the classifications include accuracy, F-measure, and confusion matrix. The F-measure is a harmonic mean of recall and precision. The F-measure includes a parameter that determines a trade-off between recall and precision. A standard F-measure is F1, which provides equal importance to recall and precision, for example. The confusion matrix, also referred to as an error matrix, provides a visualization, via a table, of performance of an algorithm such as image data processing.

In certain examples, a Radial Basis Function (RBF) kernel Support Vector Machine (SVM) can be used to classify foods based on their macromolecule content. The SVM provides a supervised learning model and associated learning algorithm to analyze data for classification and regression analysis. Given a set of classified training examples, the SVM builds a model to classify new examples according to the model of the already classified examples. The SVM classifies data by finding an optimal hyperplane to separate sets of data. However, the data cannot always be separated linearly, so an RBF kernel trick maps the data into a higher dimension to make classification easier. An RBF is a real-valued function whose value depends on a distance from an origin or center. For an RBF kernel, the kernel function is $$K(x_i, x_j) = \exp(-\gamma) \|x_i - x_j\|_2^2 \quad \text{(Eq. 2)},$$

wherein optimal values for the classifier are determined via n-fold cross validation. In Equation 2, an RBF kernel function for two center values $x_i$ and $x_j$, is defined by an exponential relationship between $x_i$ and $x_j$, as modified by gamma, γ, which quantifies a reach or span of influence for a single training example. Low gamma values indicate the influence is far, and high gamma values indicate the influence is close. The gamma value can be determined as an inverse of radius of influence of samples selected by the model as support vectors. After the optimal values are determined, the SVM classifiers are trained with these parameters and then tested on the testing data.

Figure 4:
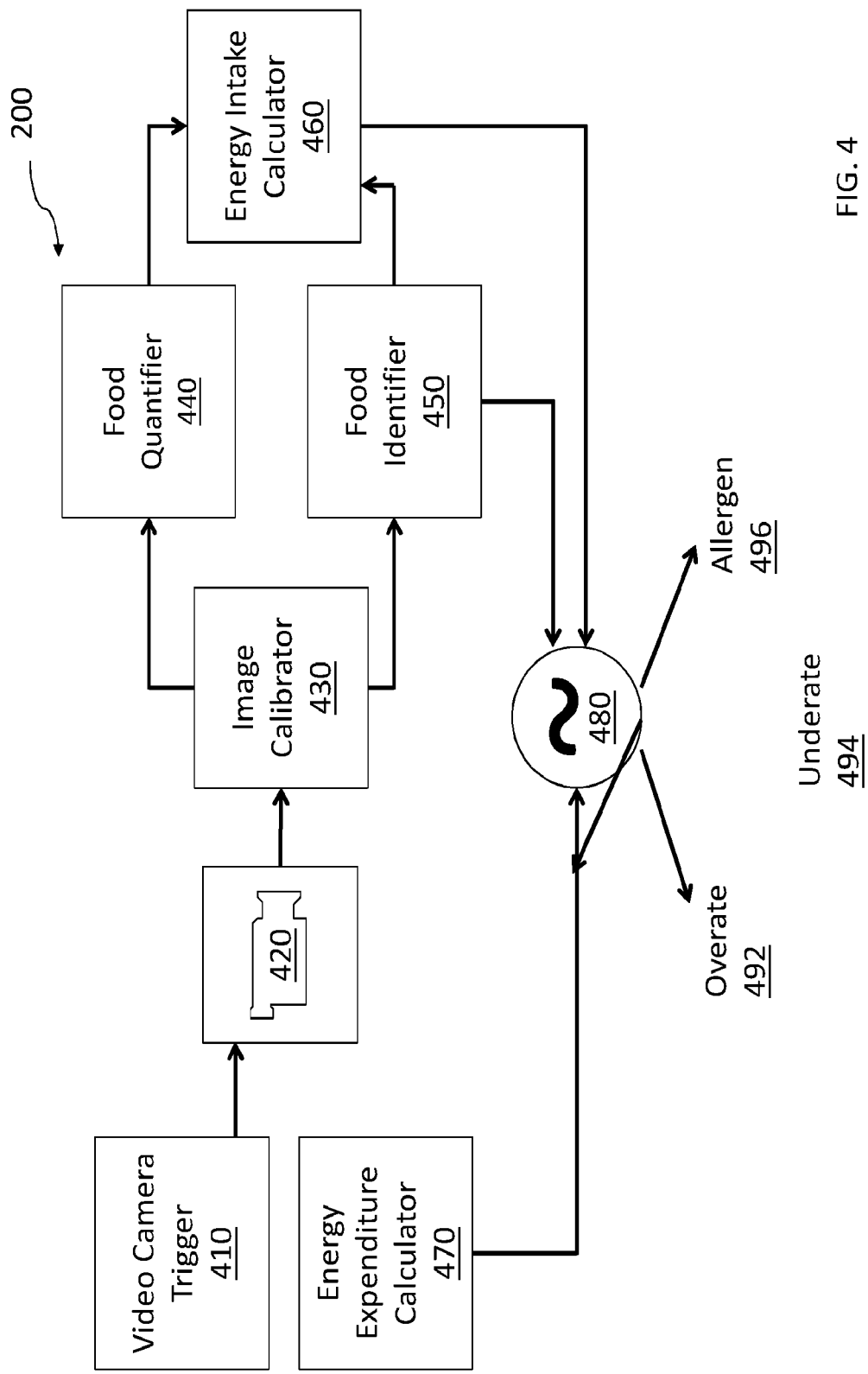
FIG. 4 illustrates further detail regarding the example hyperspectral imaging sensor system of FIG. 2.

FIG. 4 illustrates further detail regarding the example hyperspectral imaging sensor system 200. As shown in the example of FIG. 4, the system 200 includes a video camera trigger 410, camera 420, image calibrator 430, food quantifier 440, food identifier 450, energy intake calculator 460, energy expenditure calculator 470, and a data processor 480 to process the generated content and calculations to determine a dietary and/or other status of the user, such as the user over-ate 492, under-ate 494, detected an allergen 496, etc. As described further below, the example system 200 of FIG. 4 captures and analyzes, based on an activation trigger, hyperspectral and/or other image data to determine energy intake versus energy expenditure for a target individual or group of individuals and, based on the energy evaluation, determine a status of the monitored target individual(s) (e.g., the person overate 492, underrate 494, has been exposed to an allergen 496, etc.). To maintain privacy and prolong battery life, the camera 420 is triggered 410 on and off such that the camera 420 is active and capturing data when the target is eating or drinking and is otherwise off.

Figure 5:
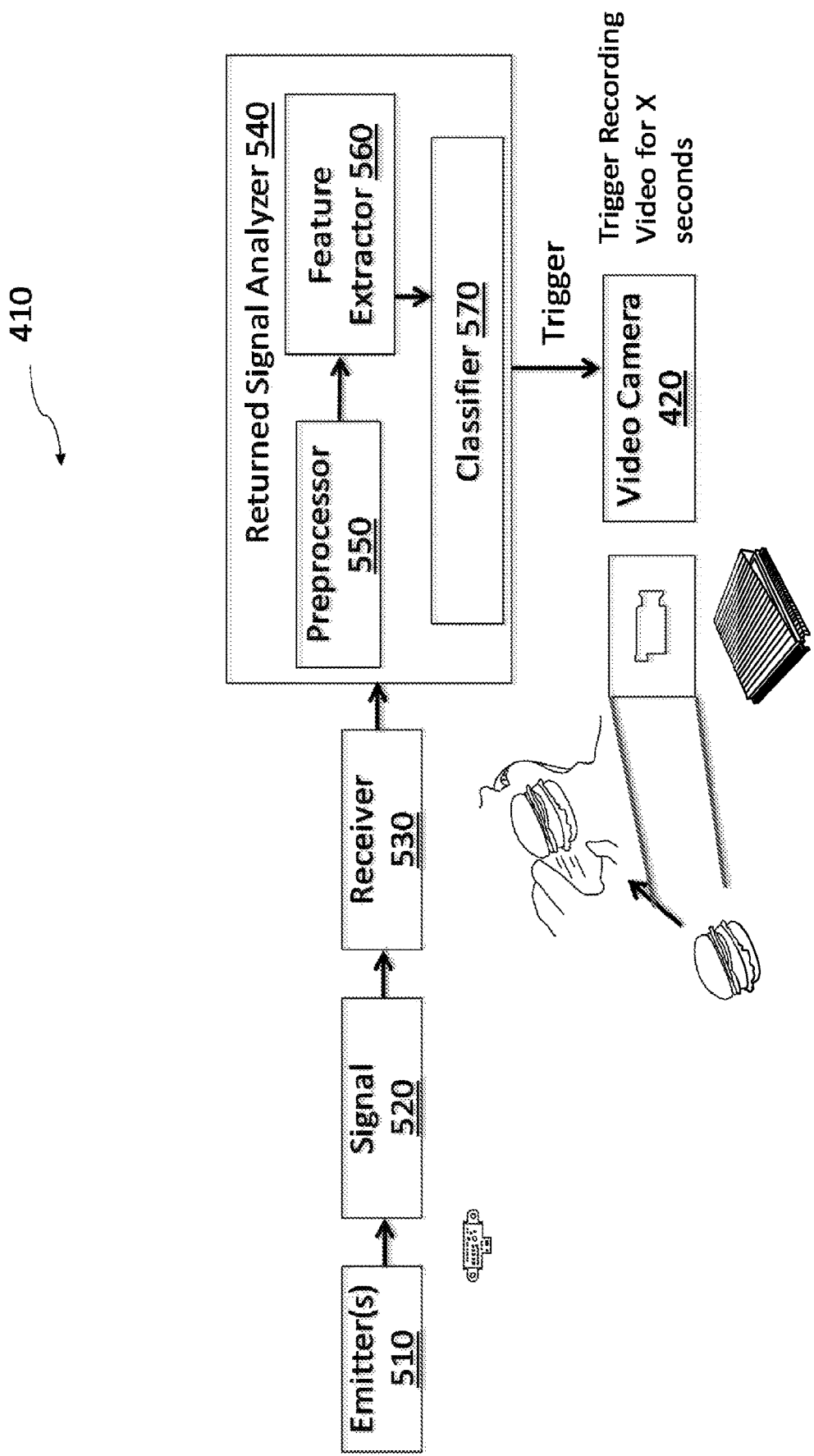
FIG. 5 depicts an example implementation of a video camera trigger.

FIG. 5 depicts an example implementation of the video camera trigger 410. Using the video camera trigger 410, battery life/energy usage can be conserved, and the camera 420 can be triggered when needed but left otherwise in an idle/sleep/power down mode, for example. The example trigger 410 includes emitter(s) 510 generating a signal 520 detected by a receiver 530 for analysis by a returned signal analyzer 540. Signal analysis by the signal analyzer 540 includes preprocessing by a preprocessor 550 and a feature extractor 560 to be supplied to a classifier 570. A resulting output from the classifier 570 forms a trigger for the video camera 420 to trigger a recording of video for a time period (e.g., X seconds such as 5 seconds, 10 seconds, 20 seconds, 30 seconds, 60 seconds, etc.).

For example, a proximity sensor can be used with a RFduino board to trigger the video camera 420. The proximity sensor works based on optical reflection, for example. An optical proximity sensor includes a light source and a sensor that detects the light. The light source generates light of a frequency that the light sensor is best able to detect, and that is not likely to be generated by other nearby sources (such as IR light, etc.). The light sensor circuit is designed so that light which is not pulsing at this frequency is rejected. The light sensor in the optical proximity sensor is a semiconductor, for example, which generates a small current when light energy strikes it. Once an object approaches the proximity sensor, there will be a peak in the trend of data. Thus, the data trend can be used, followed by preprocessing, segmentation (e.g., through energy peak detection), feature extraction and classification to validly distinguish true triggers from false triggers that may result from proximity to other objects. There are several sources for false triggers: some are dynamic triggers (e.g., a person scratching their head or face) others are static triggers (e.g., a person gets too close to the table or an object). Certain examples approach this as a two-class problem, with class 1 representing feeding gestures (or hand-to-mouth gestures), and all other gestures are represented by class 2.

Thus, in certain examples, gestures such as eating gestures, etc., and/or other movements such as swallowing, chewing, chest movement, etc., can be identified by a sensor and used to trigger operation (e.g., recording, etc.) of the video and/or still camera 420. Feeding gestures can include inertial, proximity, and/or imaging-based feeding gesture, for example. Swallow indicators can include acoustic, mechanical, electrical, and/or imaging detectors of swallowing, for example. Chewing detectors can include acoustic, mechanical, and/or imaging detectors of chewing, for example. A piezoelectric sensor can detect swallowing, chewing, etc., for example. Heart rate and heart rate variability (HRV) can also be used as a detectable trigger/feature based on electrocardiogram (ECG) chest information, light emitting diode (LED) and/or photodiode detection, imaging, etc. In certain examples, a galvanic skin response (GSR) (e.g., sweat, etc.) as detected by electrical monitoring can serve as an indicator or trigger for activity to be monitored/captured. Additionally, a determination of whether a monitored individual is alone or with others can be determined via acoustic data capture, imaging data capture, etc. In certain examples, both hyperspectral and RGB imaging data can be captured for analysis via the camera 420.

The example preprocessor 550 includes performing time stamp correction, which identifies losses in the data stream. Using dynamic-programming (e.g., a time-series alignment algorithm), knowing the ideal time stamps (e.g., given the expected sampling frequency of the signal), the actual timestamps can then be aligned properly to the ideal location. If a small amount of data is lost, interpolation (e.g., using spline interpolation) can handle missing signals. Then, data preprocessing helps ensure that the inertial signals' intended measurements were captured, primarily by smoothing to reduce noise and normalization. The premise of smoothing data is that one is measuring a variable that is both slowly varying and corrupted by random noise. Consequently, replacing each data point with an average of surrounding points reduces the level of noise, while hopefully not biasing the values. To smooth the data, a rolling mean (e.g., pandas.rolling_mean, etc.) with a window size of 100 points (e.g., approximately 3 seconds, set empirically, etc.) is applied. Then, the data is normalized using a z-score normalization technique, for example.

To segment the data, an energy signal peak detection algorithm is applied to signal whenever an object is in the field of view of the sensor. A two second window is extracted surrounding the peak, for example. Following segmentation, feature extraction 560 is applied.

Image data can be segmented to enable mapping of segmented objects in an image to images in a food database (e.g., by the food quantifier 440 and/or food identifier 450). Over-segmentation (e.g., a bag of chips is divided into two segments) and under-segmentation (e.g., the bag of chips is combined with a glass of water in one segment) can be prevented. Segmentation can be optimized and/or otherwise improved to accurately segment foods in the image using a joint iterative segmentation/classification technique in which a classifier's feedback including class label and confidence score is used to help ensure segmentation is stable. In certain examples, background pixels in an image can be distinguished from foreground pixels (e.g. using Canny operator) to detect plates, bowls, glasses, etc., and identify objects of interest. A Convolutional Neural Network (CNN) can be applied for spatial modeling and a Long Short Term Memory (LSTM) Recurrent Neural Network (RNN) can be used for temporal modeling to optimize or otherwise improve this approach.

Following data preprocessing 550 of the raw signal, features are identified and extracted to determine for which features to collect raw signal to predict an outcome. Due to the high variability across signals that represent the same activity and to help ensure that the system is capable of running in real-time, certain examples extract 11 statistical features on fixed time subdivisions of the data that are known to be useful in detecting activity, including: mean, median, max, min, standard deviation, kurtosis, interquartile range, quartile 1, quartile 3, skewness, and root mean square (RMS), for example. Following feature extraction 560, a classification technique 570 is deployed.

Once the optimal feature subset and signal processing algorithms are identified, one or more of a varied set of classification algorithms can be used including Logistic Regression (LogisticReg), AdaBoostClassifier (AdaBoost), C4.5 Decision Trees (DecisionTree), Gaussian Naive Bayes (GaussianNB), Linear Support Vector Classifier (LinearSVC), and Random Forest (RF) with n=100 trees. Both LOSOCV and 10-fold CV (averaged 10 times) can be used in certain examples. In certain examples, variability across the different runs can be calculated to help ensure that not only is the classifier with the highest F-measure (harmonic mean of precision and recall) selected, but also the classifier with the lowest variability (e.g., highest consistency) across the runs. This helps to show the consistency of the classifiers when tested on different subjects or a different test set. In certain examples, the Random Forest Classifier outperforms other algorithms in accurately distinguishing hand-to-mouth gestures from other objects in the field of view.

Figure 6:
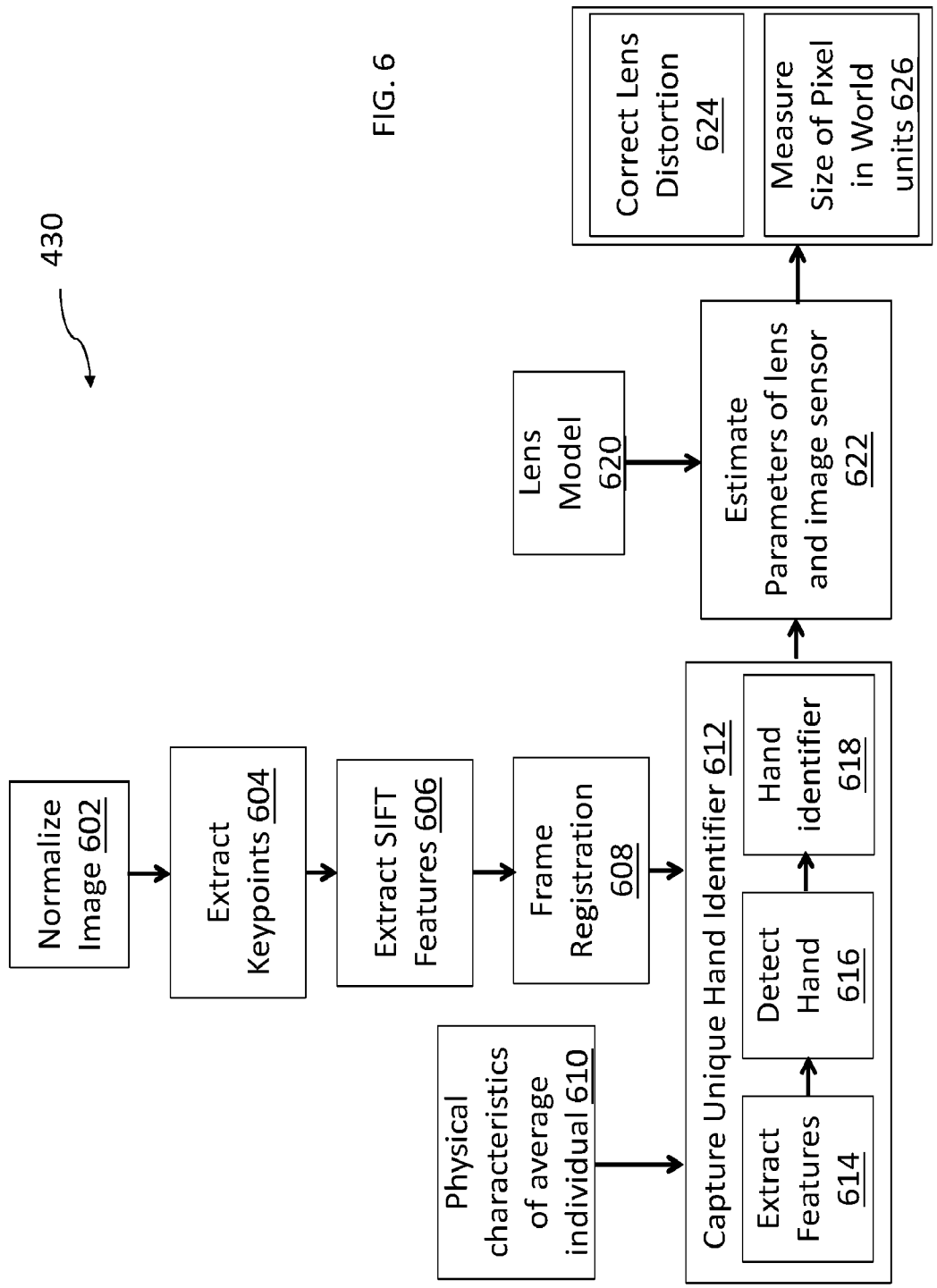
FIG. 6 depicts an example implementation of an image calibrator.

FIG. 6 depicts an example implementation of the image calibrator 430. The image calibrator 430 is to correct lens distortion, measure size of pixels in real world units, etc. In image calibration 430, a normalized image 602 is processed by the image calibrator 430 to extract key points 604. The key points 604 are processed to extract Scale-Invariant Feature Transform (SIFT) features 606, for example. The SIFT features are then used to register image frames 608 (e.g., frames from the acquired video image content, etc.).

Frame registration information 608 and physical characteristics of an average individual 610 are provided to capture a hand identifier 612 associated with the image data. The hand identifier 612 includes a feature extractor 614 to extract features for a hand detector 616, which detects the hand in the image data and generates a unique hand identifier 618, for example. The hand identifier 618 is provided with a lens model 620 to a parameter estimator 622 to estimate parameters of lens and image sensor. The parameter estimator 622 provides output(s) including a lens distortion correction 624, a pixel size measurement 626, etc.

In certain examples, a hyperspectral signature is formed from the captured image data. Rather than storing all parts of the spatial and spectral domains, a subset can be identified and stored. In certain examples, raw images are stored in a database, and unique hyperspectral signatures are used for fast database querying and indexing.

Figure 7:
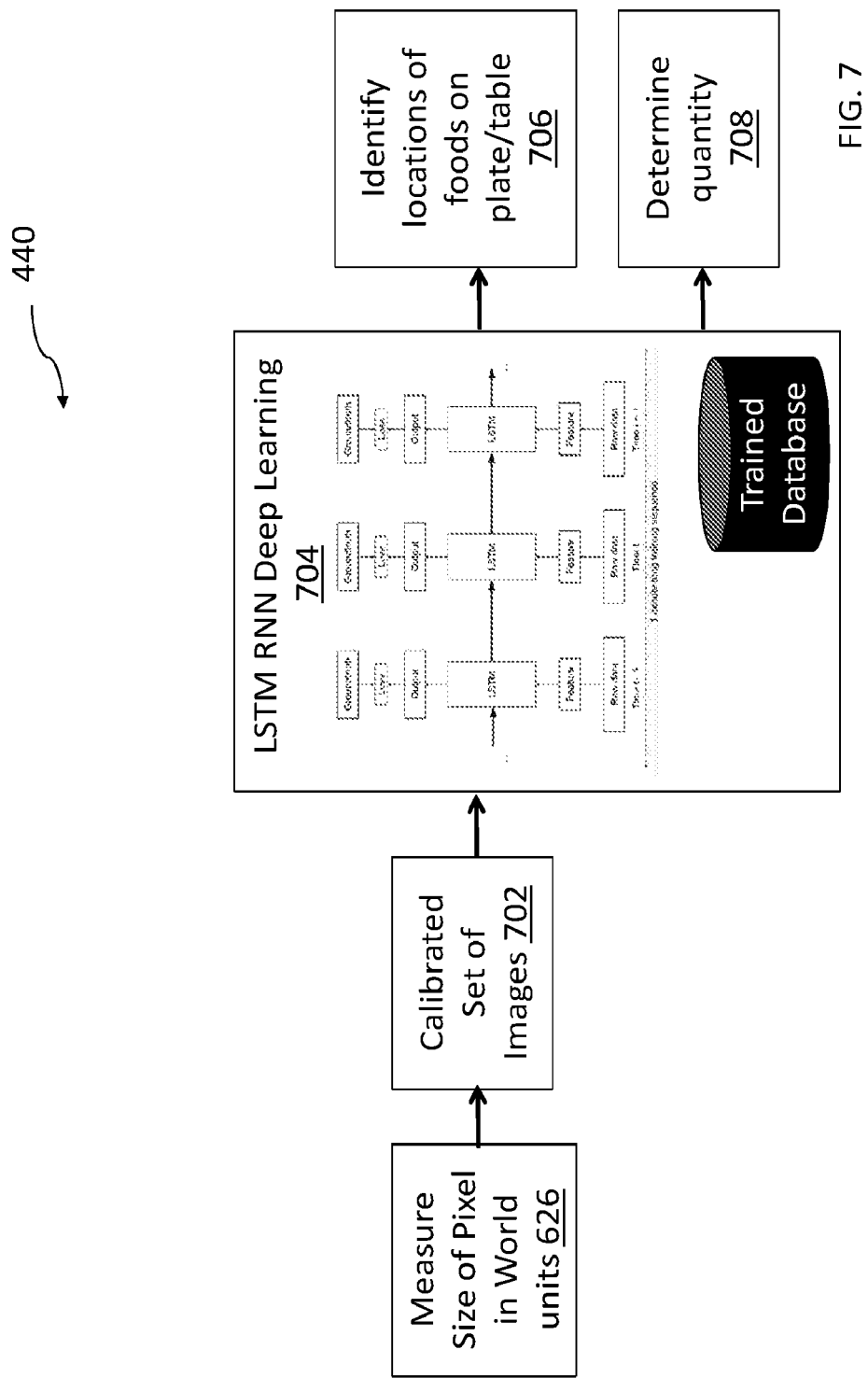
FIG. 7 depicts an example implementation of a food quantifier.

FIG. 7 illustrates an example implementation of the food quantifier 440. The example food quantification 440 quantifies each food item consumed, for example. The quantifier 440 takes the pixel size measure 626 and generates a calibrated set of images 702. The images 702 are provided to a deep learning network 704, such as a LSTM RNN deep learning network, etc. The network 704 uses the calibrated set of images 702 and its network of nodes and connections to form connections and develop a trained database, for example. Once trained, the network 704 can be deployed to identify locations of foods (e.g., on plate, table, etc.) 706, determine quantity 708, etc.

In certain examples, a small, colored checkerboard pattern is placed in the field of view of the camera 420 (e.g., attached to the bottom of the field of view of the camera 420 with respect to the part that shows the body of the wearer, etc.) to aid in calibrating for size and color of objects in a captured scene. When mapping the small checkerboard pattern with the size of an individual's thumbnail, the image data can be calibrated to determine a quantity of food near the individual's hand. The color in the patterns helps ensure the images can be normalized for the system 200 system to function under a plurality of levels of illumination (e.g., light or dark).

For example, hyperspectral sensors collect information as a set of images. The images with the essential spectral bands are extracted and fed into a recurrent neural network (RNN) model 704, which is designed specifically for sequential data. RNN models 704 can be trained on one set of input sequence, and then generalized to a different length test sequence, for example. The RNN 704 achieves this property through the inclusion of cycles in its computation graph, as well as sharing of parameters across time, for example.

A particular implementation of the RNN 704 is utilized to capture locations of food 706 and to determine the quantity of food 708 from the continuous data stream of the video feed, for example. First, supervised sequence labeling models are used from existing image data using Hyperspectral Imaging, where the output sequence has the same length as the input sequence. Second, long short-term memory (LSTM) is used as the recurrent layer to avoid the vanishing gradient problem common when applying RNN.

LSTM has been employed successfully in many applications related to sequential data such as speech recognition, video action recognition, and wearable action recognition. A complicated model can be built with multiple recurrent and constitutional layers. The neural network model SwallowNet is designed to have a single, but most likely several, recurrent layers combined with one nonlinear transformation layer for feature extraction, for example.

In certain examples, the data stream is split into chunks representing each essential spectral band. Each image is then split into chunks representing portions of the image for the system to learn whether these chunks from this band represent food or not. These chunks are then transformed through a nonlinear embedding layer which resembles feature extraction, for example. The network learns the optimal representation to differentiate between food and no food.

Features are then fed into an LSTM layer to learn the temporal dynamics of the signals. An LSTM layer has internal state and output, which are updated recurrently throughout the sequence. LSTM utilizes forget gates, input gates and output gates to implement this update, for example.

From these gates, the internal states and output can be obtained. Outputs from LSTM layers are transformed through another linear transformation layer to obtain two dimensional outputs for each chunk, for example. The loss of the network is then calculated as the cross-entropy loss between ground truth and the soft-max activation of the output layer summed over the whole sequence, for example.

The RNN 704 can be trained on images from each spectral band, for example. If not enough data is present, data augmentation can be performed from existing data. At each iteration, images and their corresponding labels are fed into the optimization. In certain examples, to increase the training set, data augmentation is used by scaling the sequences by a random number between 0.8 and 1.2. This range is selected empirically to introduce realistic noise into the data, while not drastically distorting signal shape.

A dimension of the embedding layer is selected to compress the original data. The dimension of LSTM layer is set. The network 704 is trained using the Adam optimization algorithm with a learning rate of 1e-3, for example. A number of training iterations is fixed throughout the process. A backpropagation through time algorithm updates both feature representation and LSTM weights at each optimization iteration, instead of training each layer separately, for example.

Figure 8:
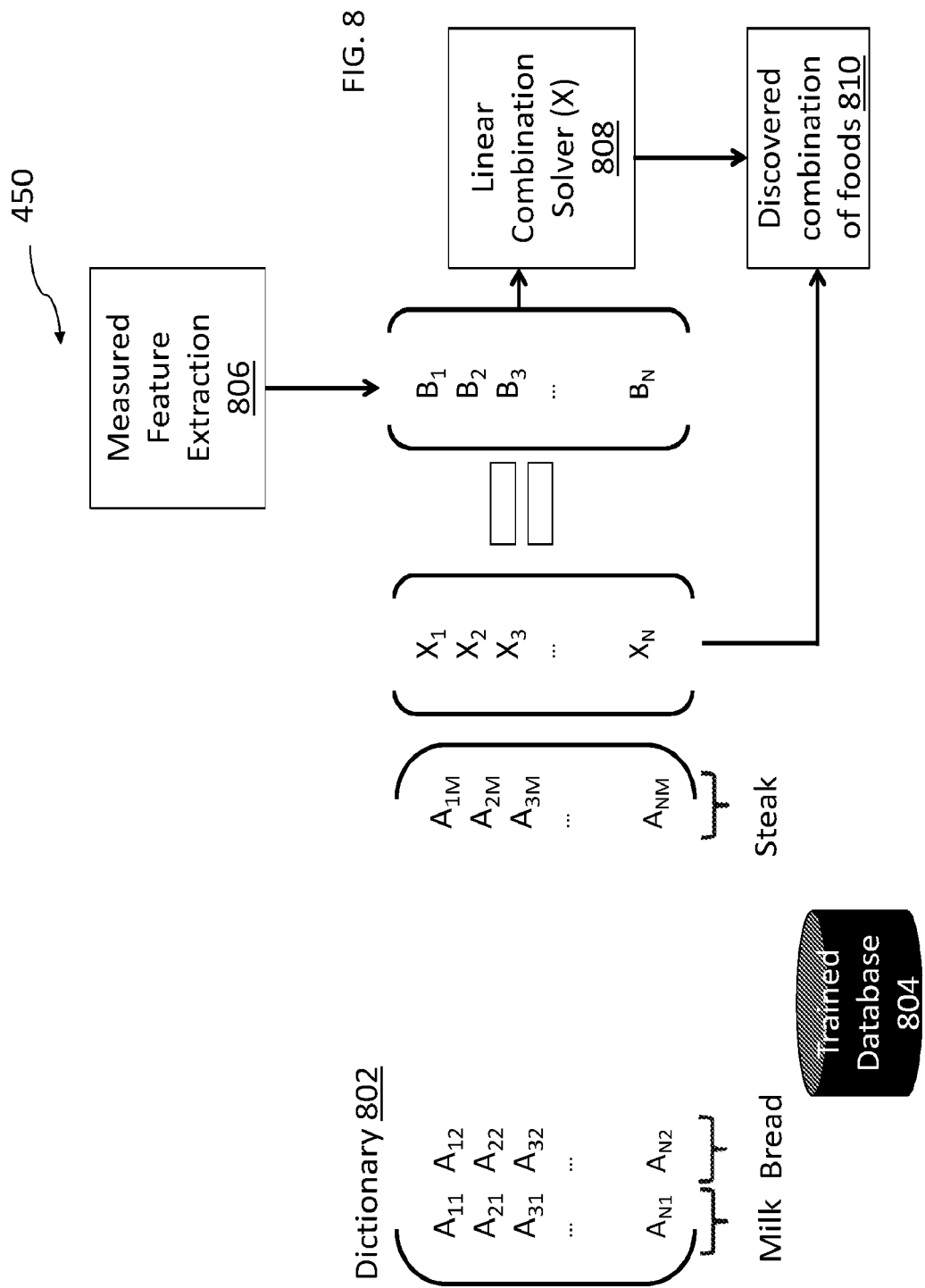
FIG. 8 depicts an example implementation of a food identifier.

FIG. 8 illustrates an example implementation of the food identifier 450. The food identification 450 is to determine a probability of each food item on a monitored plate, for example. The food identification 450 can be based on a sparse representation of data, for example.

As shown in the example of FIG. 8, a dictionary 802 forms a trained database 804 based on characteristics spectrally identifying one or more food ideas. The food item characteristics are processed with respect to measured feature extraction 806 information and provided to a linear combination solver 808. The solver 808 solves for X to discover a combination of food items 810 present in the image field of view, for example.

Machine learning algorithms such as a Random Forest classifier, etc., can be used to classify foods. In certain examples, such algorithms are optimized or otherwise improved further using sparse signal representation to obtain compact high-fidelity representation of the observed food item and to extract semantic information using unique signatures across multiple wavelengths of the spectrum. In certain examples, hyperspectral images are combined with existing RGB imagery databases. In certain examples, such databases are enriched with spectral and audio signatures. Unknown food items can be detected early in the development phase to populate and advance food databases with new foods, for example.

Figure 9:
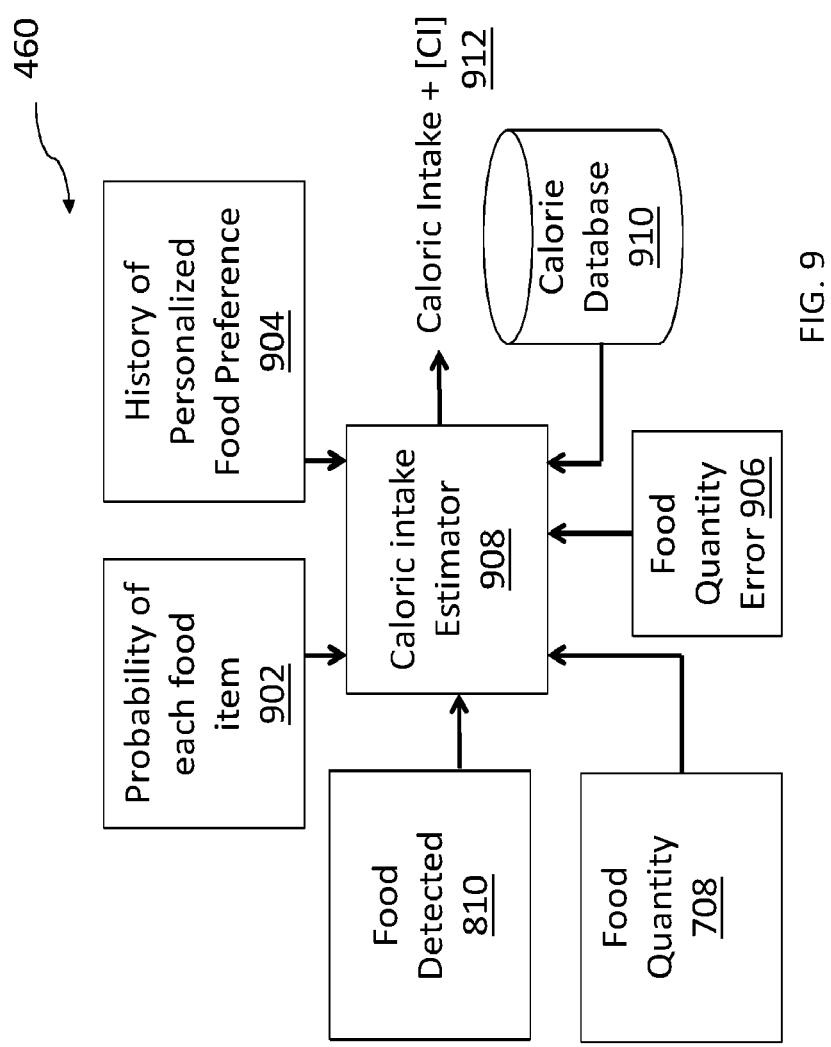
FIG. 9 depicts an example implementation of an energy intake calculator.

FIG. 9 illustrates an example implementation of the energy intake calculator 460 to determine calories consumed from a meal, bites, etc. As shown in the example of FIG. 9, a probability of each food item 902 and a history of personalized food preference 904 are provided with an indication of food detected 810, food quantity 708, and a food quantity error 906 to a caloric intake estimator 908. The caloric intake estimator 908 processes the food information 708, 810 902, 904, 906 and leverages a calorie database 910 to generate a caloric intake value 912.

In certain examples, the caloric intake estimator 908 takes into account foods detected 810 and food quantity 708, along with food quantity error 906, probability of each food item 902, and history of personalized food preference (e.g., what foods does this individual eat/not eat, etc.) 904, and input from the calorie database 910 and generates the Caloric intake estimate 912 with a confidence interval (CI).

In certain examples, the energy intake calculator 460 determines which parts of the spectrum to use to improve/optimize determination of nutrients and caloric content. In addition to distinguishing between calorie levels, the energy intake calculator 460 can determine whether food content is low/med/high salt, sugar, fat, protein, and/or carbohydrate, etc. Each spectrum provides unique information that will enable the system 200 to adjust levels based on the food type identified (e.g., by the food identifier 450).

In certain examples, an inertial motion unit (IMU) can be used in frame registration to help align hyperspectral frames across time during user movement.

In certain examples, the energy intake calculator 460 implements an energy intake algorithm to combine each identified food item and associated confidence rating and quantity to estimate a number of calories of each food segment identified on each plate. A first type of algorithm identifies a number of calories at the beginning and end of the meal, which helps determine foods consumed during the entire meal. A second type of algorithm tracks foods that move from the hand to the mouth and estimates calories accordingly.

Figure 10:
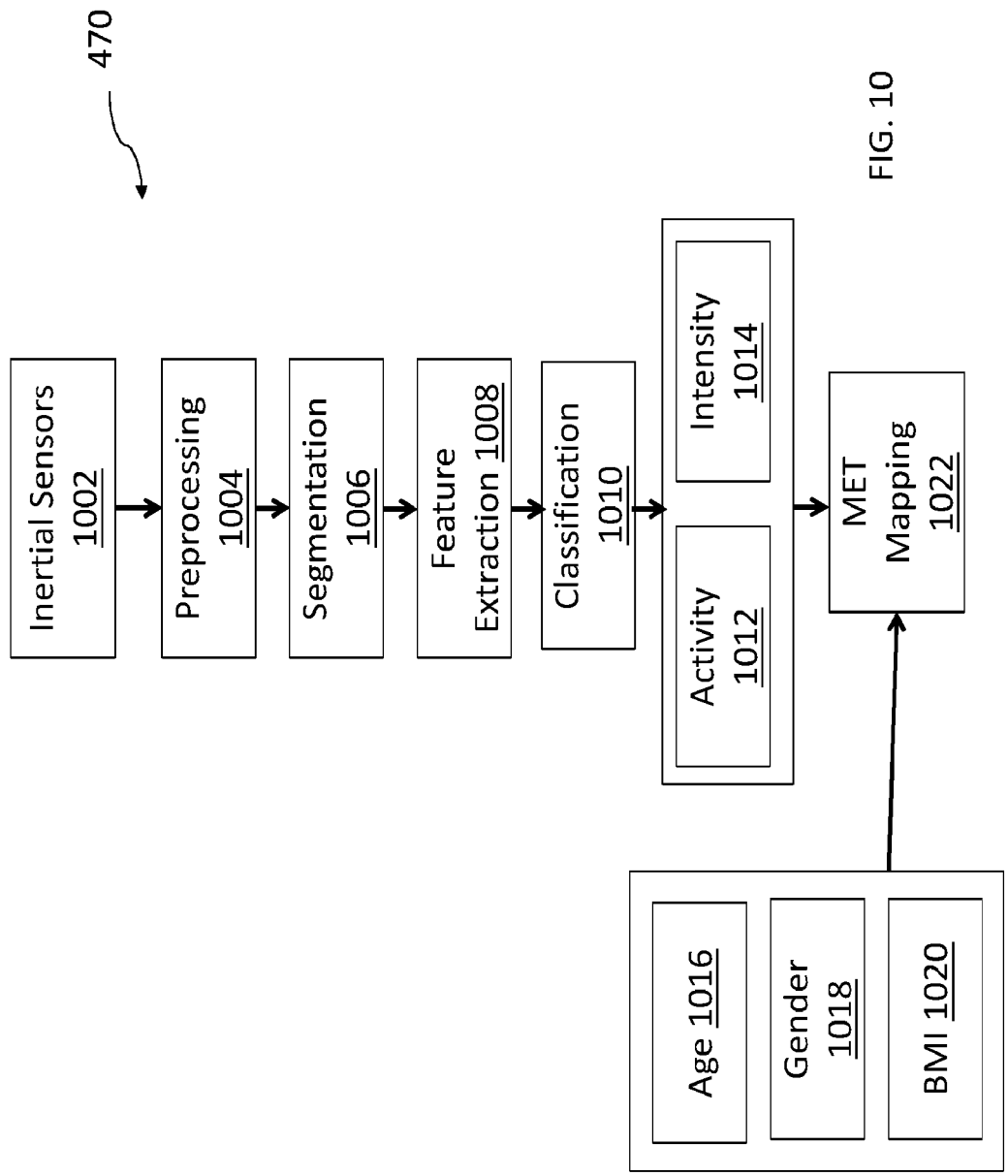
FIG. 10 depicts an example implementation of an energy expenditure calculator.

FIG. 10 illustrates an example implementation of the energy expenditure calculator 470. The energy expenditure calculator 470 determines caloric expenditure by calculating a metabolic equivalent of task(s) using inertial body sensors, such as a triaxial accelerometer, gyroscope, magnetometer, etc. As shown in the example of FIG. 10, inertial sensor(s) 1002 provide position/motion information with image data for preprocessing 1004 and segmentation 1006. From the preprocessed and segmented information, feature extraction 1008 can generate features for classification 1010. Classification 1010 generates an indication of activity 1012 and an intensity 1014 associated with that activity 1012. Activity 1012 and intensity 1014 information can be combined with demographic information such as age 1016, gender 1018, and body mass index (BMI) 1020 to form a Metabolic Equivalent of Task (MET) mapping 1022. The MET, or metabolic equivalent, is a physiological measure quantifying an energy cost of physical activities defined as a ratio of a) metabolic rate (a rate of energy consumption) during a specific physical activity to b) a reference metabolic rate. The MET mapping 1022 is provided to the data processor 480 with caloric intake estimation information 912 to generate an outcome 490-494.

Once the food has been identified and energy intake and expenditure have been calculated, a state of the monitored individual can be determined. For example, a histogram of food consumed for 1-2 meals can be determined and compared to a 1 z-score cutoff or threshold to evaluate whether the target is overeating (e.g., over the threshold), undereating (e.g., under the threshold), etc. For example, salt intake can be estimated based on food identification and energy intake. Food identification can be used to determine whether the monitored, target individual ate a snack versus a full meal and whether the individual has one overeating meal in a day versus multiple overeating. A meal plan can be adjusted, prescription issued, and/or other intervention triggered if the analysis indicates a pattern of overeating, undereating, etc.

The z-score indicates a distance of a number from the mean of a normally distributed data set. A 1 z-score is within one standard deviation of the mean. Thus, if the mean defines a "normal" meal, then a caloric/energy outcome that is more than one standard deviation above the mean indicates overeating, and an outcome that is more than one standard deviation below the mean indicates undereating. Thus, if a participant p consumes n eating episodes (e.g., meals/snacks) for 14 days, then a personalized caloric distribution model is created and converted to a standard normal distribution. For an eating episode i during day d, $E_i^d(x)$ is considered overeating if the determined caloric intake $Ci(x)>1$ z-score (e.g., 85.1% percentile, etc.) threshold of participant p's personalized caloric intake distribution, which indicates larger than normal meals typically consumed by the participant.

Figure 11:
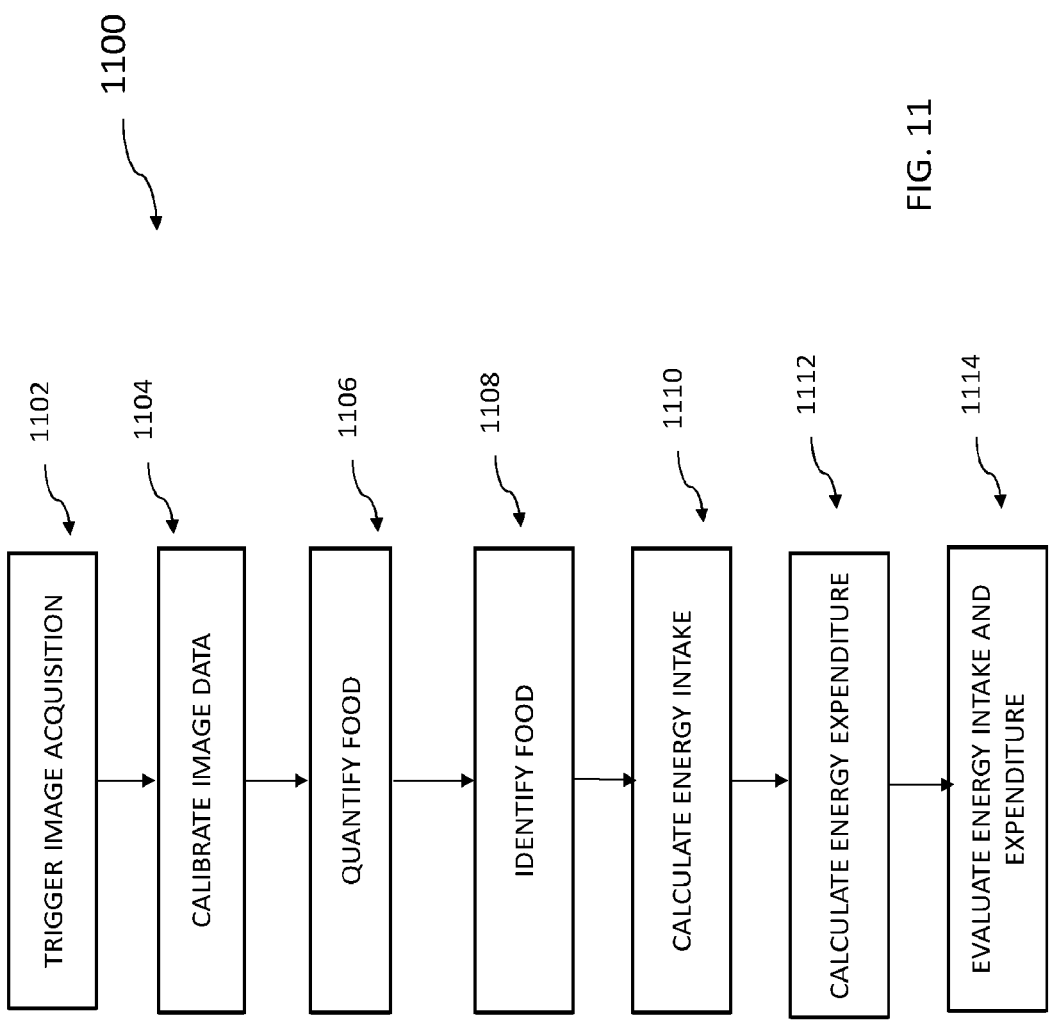
FIG. 11 show a flow diagram of an example method of hyperspectral image analysis using the example system of FIGS. 4-10.

FIG. 11 illustrates a flow diagram of an example method 1100 of hyperspectral image analysis using the example system 200. At block 1102, image acquisition is triggered. For example, a sensor can trigger 410 acquisition by a video and/or other imaging camera 420. At block 1104, acquired image data is calibrated 430. At block 1106, food detected in the image data is quantified 440, and, at block 1108, the food is identified 450. At block 1110, energy intake is calculated 460. At block 1112, energy expenditure 470 is calculated. At block 1114, an evaluation is generated 480 based on the energy intake calculation 460 and the energy expenditure calculation 470. Output can include an evaluation of overeating 490, under-eating 492, presence of allergen 494, etc.

Figure 12:
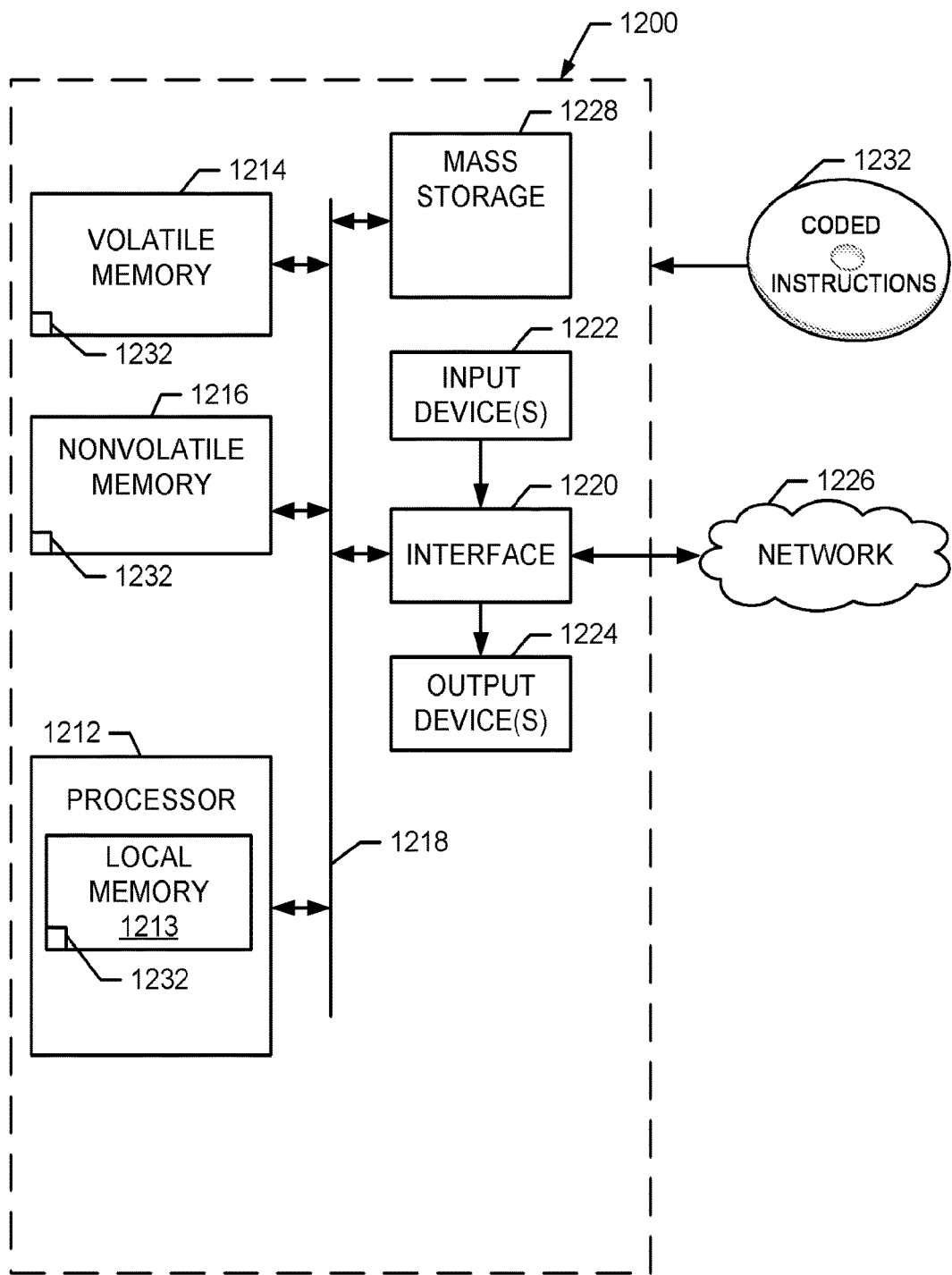
FIG. 12 is a block diagram of an example processor platform 1200 capable of executing instructions to implement the example apparatus, systems and methods disclosed and described herein.

FIG. 12 is a block diagram of an example processor platform 1200 capable of executing instructions to implement the example apparatus, systems and methods disclosed and described herein. The processor platform 1200 can be, for example, a server, a personal computer, a mobile device (e.g., a cell phone, a smart phone, a tablet such as an IPAD™) a personal digital assistant (PDA), an Internet appliance, or any other type of computing device.

The processor platform 1200 of the illustrated example includes a processor 1212. Processor 1212 of the illustrated example is hardware. For example, processor 1212 can be implemented by one or more integrated circuits, logic circuits, microprocessors or controllers from any desired family or manufacturer.

Processor 1212 of the illustrated example includes a local memory 1213 (e.g., a cache). Processor 1212 of the illustrated example is in communication with a main memory including a volatile memory 1214 and a non-volatile memory 1216 via a bus 1218. Volatile memory 1214 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 can be implemented by flash memory and/or any other desired type of memory device. Access to main memory 1214, 1216 is controlled by a memory controller. The processor 1212, alone or in conjunction with the memory 1213, can be used to implement all or part of the apparatus, systems, and/or methods disclosed herein.

Processor platform 1200 of the illustrated example also includes an interface circuit 1220. Interface circuit 1220 can be implemented by any type of interface standard, such as an Ethernet interface, a universal serial bus (USB), and/or a PCI express interface.

In the illustrated example, one or more input devices 1222 are connected to the interface circuit 1220. Input device(s) 1222 permit(s) a user to enter data and commands into processor 1212. The input device(s) 1222 can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to interface circuit 1220 of the illustrated example. Output devices 1224 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 1220 of the illustrated example, thus, typically includes a graphics driver card, a graphics driver chip or a graphics driver processor.

Interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

Processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile disk (DVD) drives.

Coded instructions 1232 associated with any of the examples disclosed and described herein can be stored in mass storage device 1228, in volatile memory 1214, in the non-volatile memory 1216, and/or on a removable tangible computer readable storage medium such as a CD or DVD.

It may be noted that operations performed by the processor platform 1200 (e.g., operations corresponding to process flows or methods discussed herein, or aspects thereof) may be sufficiently complex that the operations may not be performed by a human being within a reasonable time period.

Figure 13:
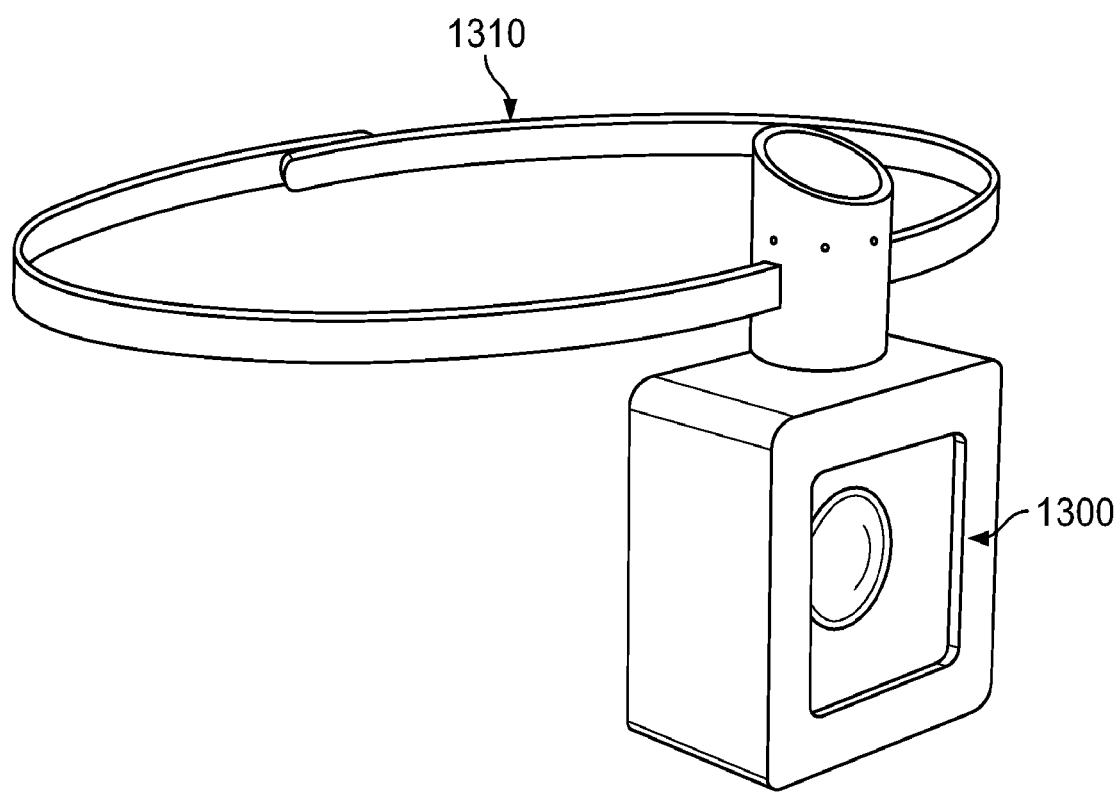
FIG. 13 shows an example snapshot imager apparatus.

As shown in FIG. 13, a snapshot imager 1300 can be mounted on a necklace, strap, etc. 1310 to gather, process, and transmit imaging and other sensor data for caloric and/or other energy analysis. The snapshot imager 1300 is a nutrient detector that captures visible (e.g., 470-630 nm) and/or near infrared (e.g., 600-1000 nm) light in 16 visual bands and/or 25 near infrared bands, for example. The example snapshot imager 1300, like the camera 420, provides an imager, lens, battery/power, and data transfer connection to capture image data and transfer data to the rest of the system 400 (e.g., to the image calibrator 430 to be processed and provided to the food quantifier 440 and the food identifier 450) for processing and analysis. The imager 1300 can integrate spectral filters 'per pixel' monolithically on top of image wafers in a mosaic pattern, for example. The mosaic pattern allows multispectral imaging at video rates in a small form factor. Particular spectral bands can be identified for use in image data capture, for example.

In certain examples, the snapshot imager 1300 can include a microphone to establish a unique signature for each food to complement its spectral signature. For example, a beamforming microphone array can be used with background noise cancellation to help ensure high quality in noisy environment. The camera, microphone, and/or other sensor(s) can be integrated on one or more printed circuit boards, processors, etc., in the imager 1300, for example.

Figure 14:
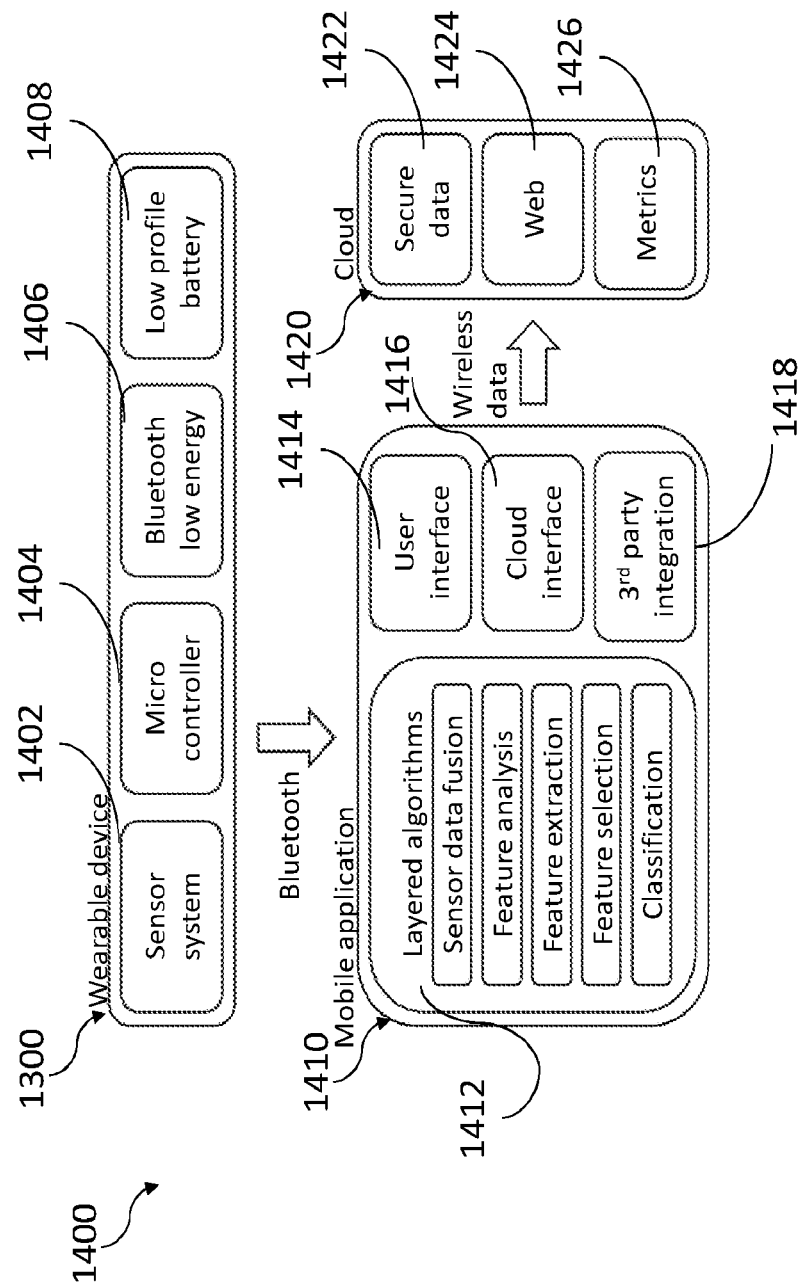
FIG. 14 depicts an example mobile infrastructure to communicate and process data from a wearable device to a cloud-based infrastructure.

The example snapshot imager 1300 can be part of an architecture 1400 including a mobile application 1410 communicating with a cloud-based infrastructure 1420, such as shown in the example of FIG. 14. The example snapshot imager 1300 is implemented as a wearable device including a sensor system 1402 (e.g., a camera, microphone, proximity sensor, etc.), a microcontroller or other processor 1404, a Bluetooth Low Energy (BLE) and/or other communication interface 1406, and a battery (e.g., a low profile battery, etc.) 1408.

The wearable sensor/imaging device 1300 communicates (e.g., via Bluetooth, WiFi, Near Field Communication (NFC), etc.) with a mobile application 1410 to process the acquired image and/or other sensor data from a target user. The mobile application 1410 includes a plurality of layered algorithms 1412 to process the image/sensor data including sensor data fusion, feature analysis, feature extraction, feature selection, and classification. The mobile application 1410 also includes a user interface 1414 to allow a user to interact with the mobile application 1410 and associated functionality 1412, data, etc. The mobile application 1410 also includes a cloud interface 1416 to send data to and/or request data from the cloud-based infrastructure 1420. The mobile application further includes third party integration 1418 for one or more third party applications, platforms, etc.

The cloud-based infrastructure or platform 1420 includes secure data storage 1422 to store data from the mobile application 1410 and/or aggregate that data with data from other sources (e.g., other wearable device(s) 1300, information system(s), etc.). The cloud infrastructure 1420 includes a Web service 1424 to display and provide interaction with processed data, etc., via the Web. The cloud infrastructure 1420 also includes one or more metrics 1426 computed and stored to evaluate individual, group, and/or other aggregate target behavior, intervention, etc.

In the example of FIG. 14, sensor(s) 1402 transmit data to the microcontroller board 1404, which filters the data and uses the radiofrequency (RF) (e.g., BLE, etc.) transceiver to transmit the data to the mobile platform 1410. The mobile platform 1410 fuses data from the sensors and extracts one or more features. A subset of features is used to classify food type, associated calories, etc. Feedback can then be provided to a user.

Thus, certain examples provide wearable sensors (e.g., neck-worn camera, etc.) and associated processing systems to determine caloric and nutrient intake. Certain examples enable monitoring of an individual, group, population, etc. Certain examples determine caloric and nutrient intake in a particular patient/user context and provide feedback.

In certain examples, chewing can be detected using a proximity sensor arranged in the imager 1300 near a target user. Additionally, an IMU can be provided in the device 1300 that identifies leaning of the target user and extrapolates whether the user is leaning to eat or drink (e.g., chew, swallow, etc.). Image data can be segmented and candidates selected using a linear-time approximation algorithm, for example. In certain examples, features from three signals, gradient boosting, and time point fusion enable capture of eating episodes for analysis. Thus, the example device 1300 can include an IMU, light sensor, proximity sensor, as well as a camera to capture information from a target and relay the information for processing, for example.

Figure 15A:
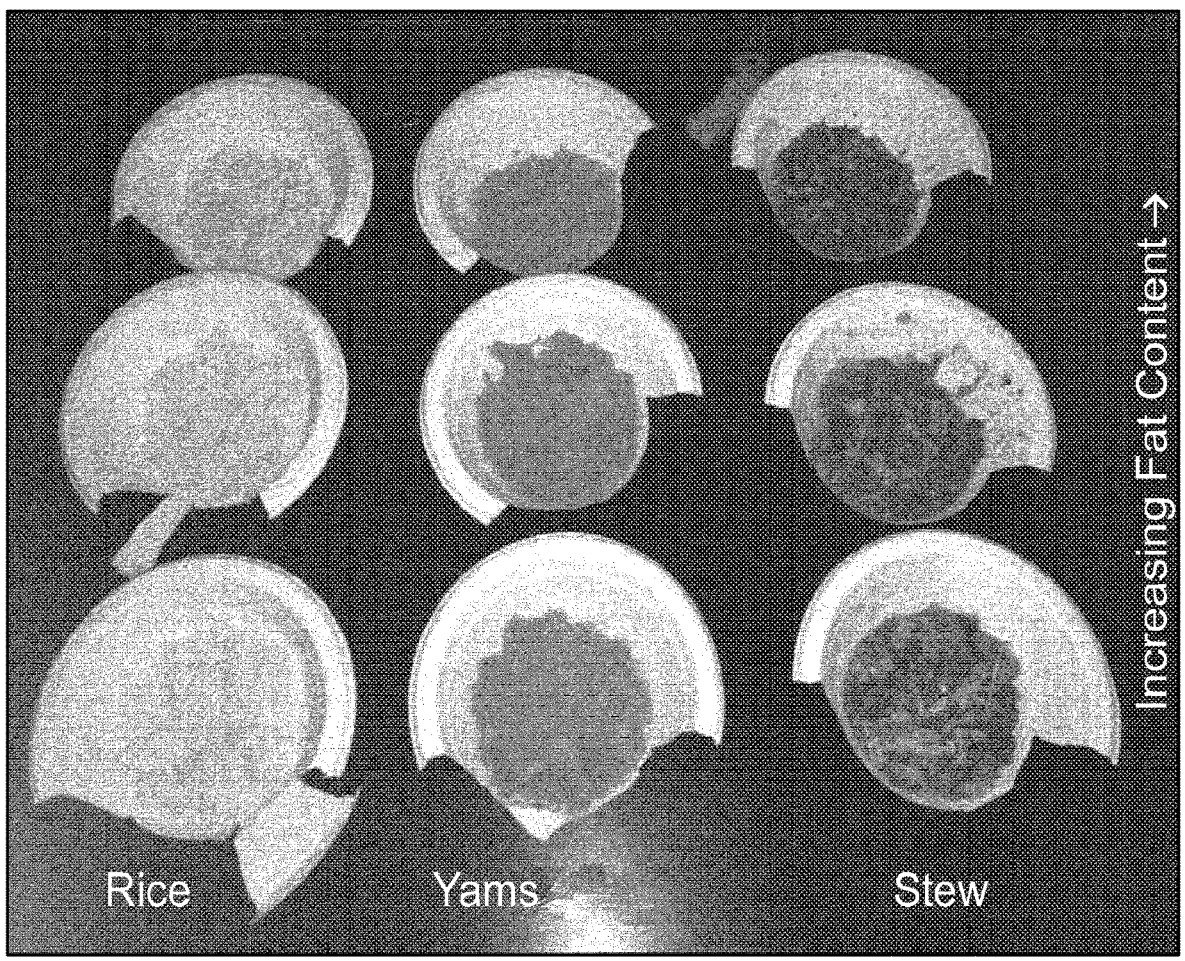
FIG. 15A depicts example food samples that can be imaged and analyzed for caloric content and composition.
Figure 15B:
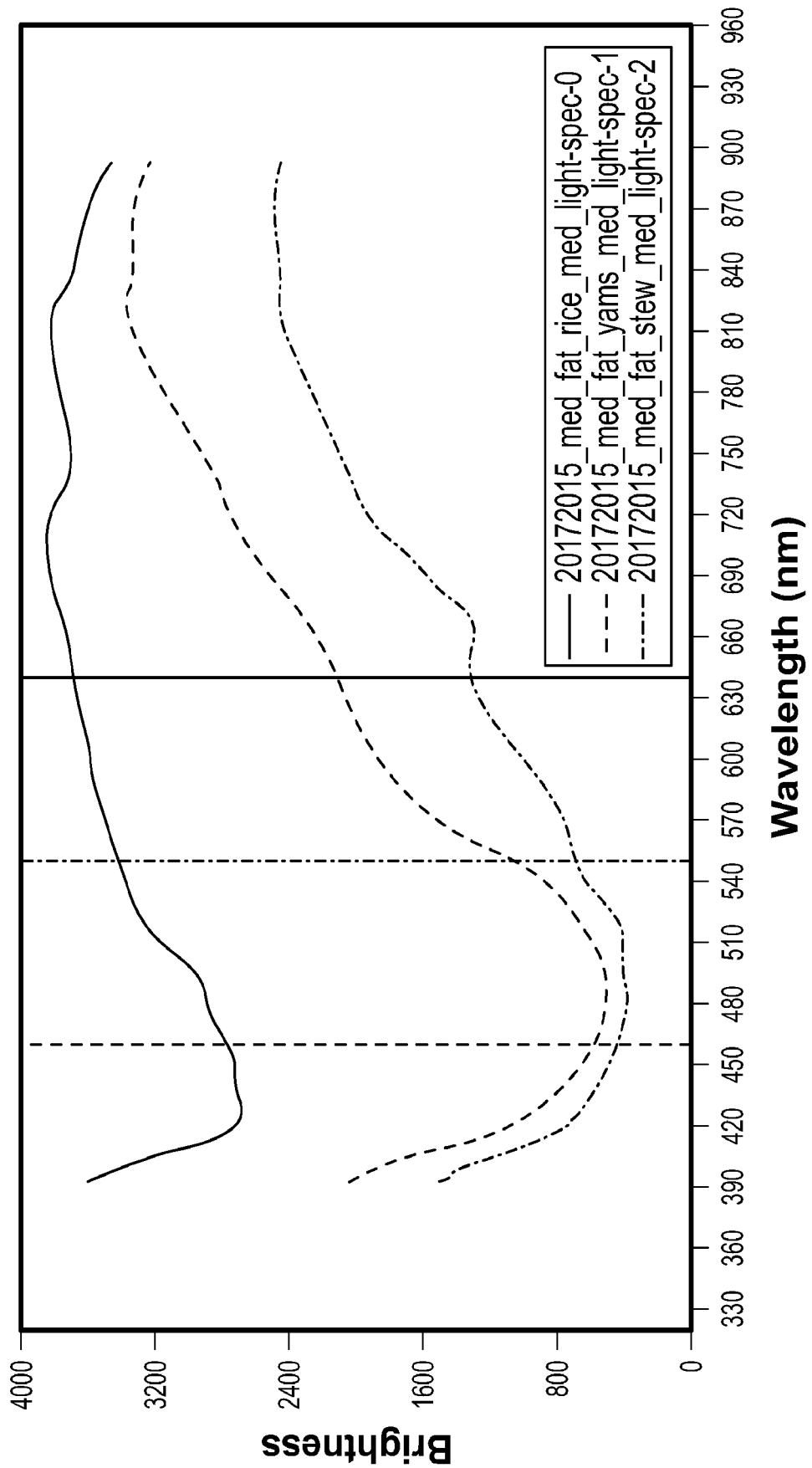
FIG. 15B depicts example food items differentiated based on their associated spectrum characteristics.
Figure 15C:
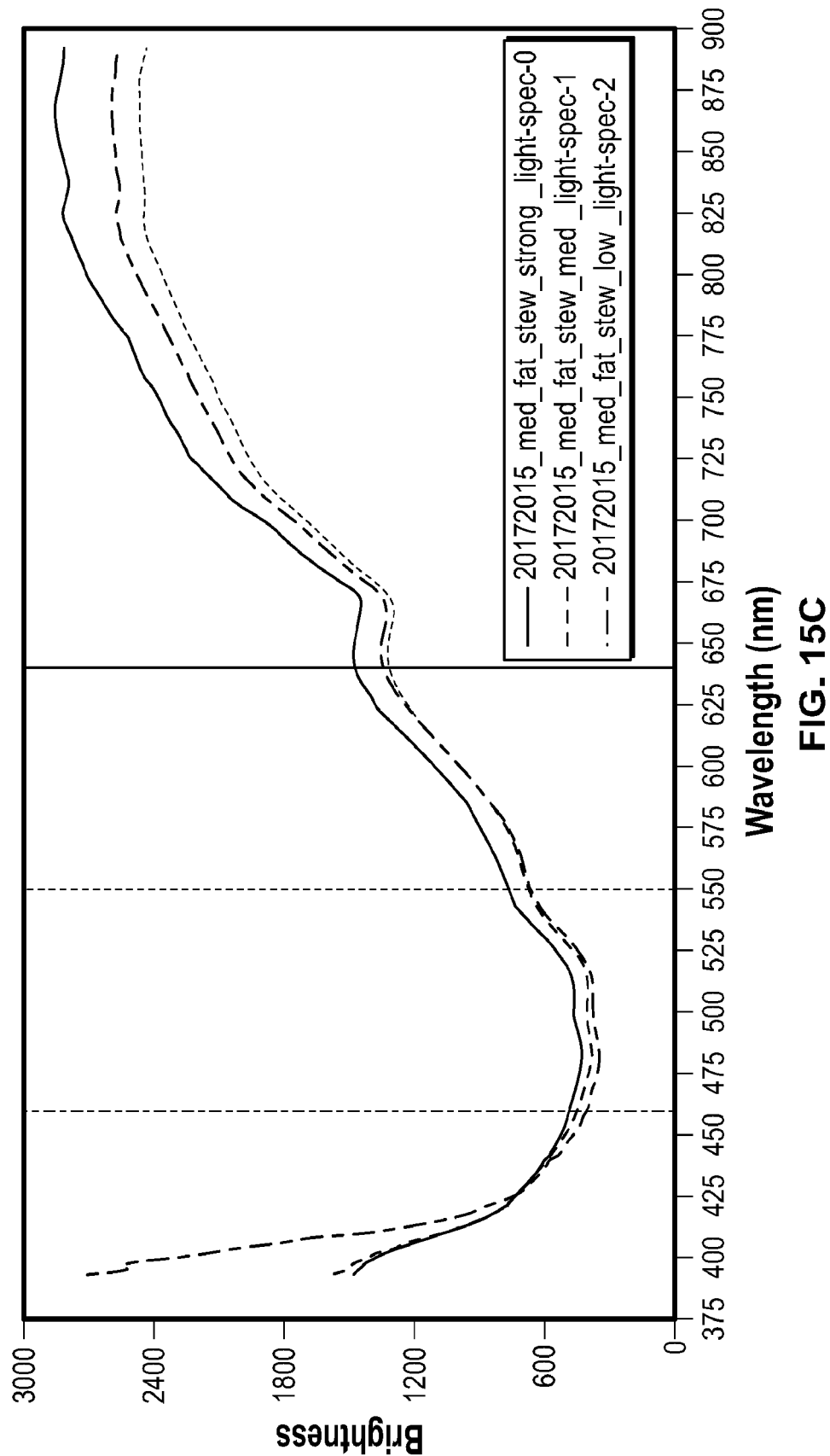
FIG. 15C depicts spectra associated with stew having medium fat images in three different light conditions.
Figure 15D:
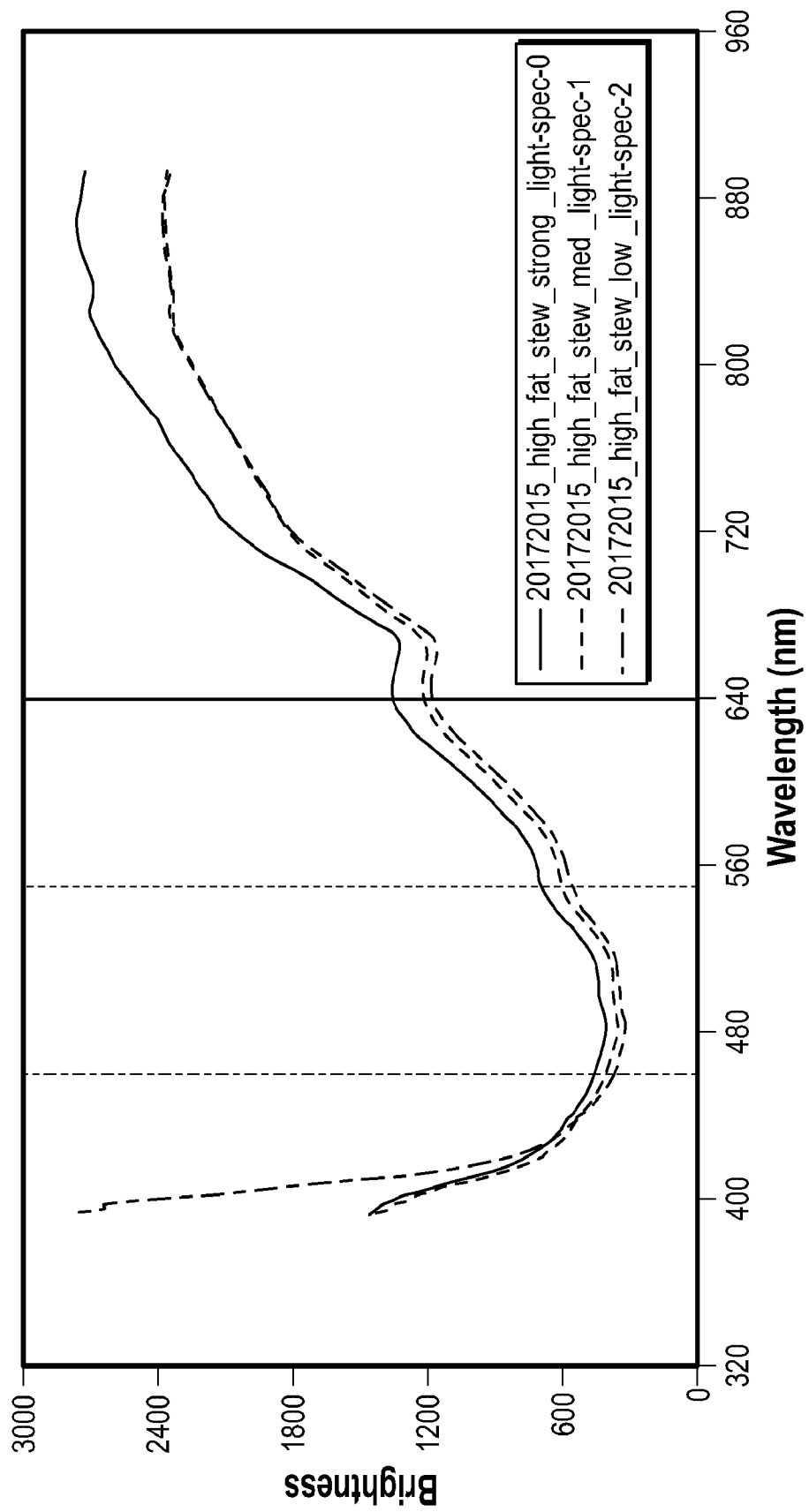
FIG. 15D depicts spectra associated with stew having high fat images in three different light conditions.

FIG. 15A illustrates example food samples that can be imaged and analyzed for caloric content and composition according to the apparatus, systems, methods, etc., described above. FIG. 15B shows an average spectrum for three kinds of food items under the same light condition and fat content. As demonstrated by the example of FIG. 15B, the food items can be differentiated based on their associated spectrum characteristics. FIGS. 15C and 15D illustrate spectra associated with stew having medium (FIG. 15C) and high (FIG. 15D) fat images in three different light conditions. Differences in spectra can be identified based on the intensity of light.

FIG. 16 illustrates a table showing results of food calorie content identification using RGB and hyper-spectral image analysis. As shown in the example table of FIG. 16, hyperspectral image analysis produces improved accuracy with better precision and recall compared to RGB image analysis. Particularly with yams (increase from 65.83% to 81.66%) and stew (increase from 54.44% to 82.77%), the hyperspectral image analysis demonstrates significantly improved accuracy. Precision and recall are similarly improved.

Recall (sensitivity) is a likelihood that an item will be correctly identified (e.g., a likelihood that a low-sugar banana dish will be correctly identified as containing a low level of sugar, etc.). Precision is a probability that a dish identified with a certain characteristic (e.g., a dish identified as containing low sugar, etc.) actually has that characteristic (e.g., actually contains a low level of sugar).

FIG. 17 shows an example confusion matrix including labels classified using one or more SVMs. FIG. 17 provides true labels, classified labels, sensitivity/recall, and associated precision and accuracy, along with an F1 score. False negatives are samples which were incorrectly identified as belonging to a different sugar level. Since this is not binary classification in a 2×2 matrix there is no false positive metric. The F1 Score is a harmonic mean between precision and recall, and accuracy is a number of correctly identified samples divided by the total number of samples.

FIGS. 18A-18B show example confusion matrices for hyperspectral (FIG. 18A) and RGB (FIG. 18B) image data and analysis. As indicated on the far right of each matrix, accuracy jumps from 47% using RGB data analysis to 91% accuracy using hyperspectral data analysis.

FIG. 19 shows an example of F-measures obtained for classification of fat in eggs using hyperspectral analysis alone, RGB analysis alone, or a fused hyperspectral/RGB analysis. Thus, hyperspectral image analysis, alone or in combination with RGB image data analysis, enables food identification and determination of associated caloric content. A target individual's caloric intake can then be determined and compared to their caloric expenditure. While RGB narrows colors to a single red, green, or blue value, hyperspectral imaging captures an intensity level of all wavelengths in a spectrum. Thus, hyperspectral imaging of RGB image data can provide a range of reds, greens, and blues, for example. RGB information can be augmented with hyperspectral image data to provide improved results.

Figure 20:
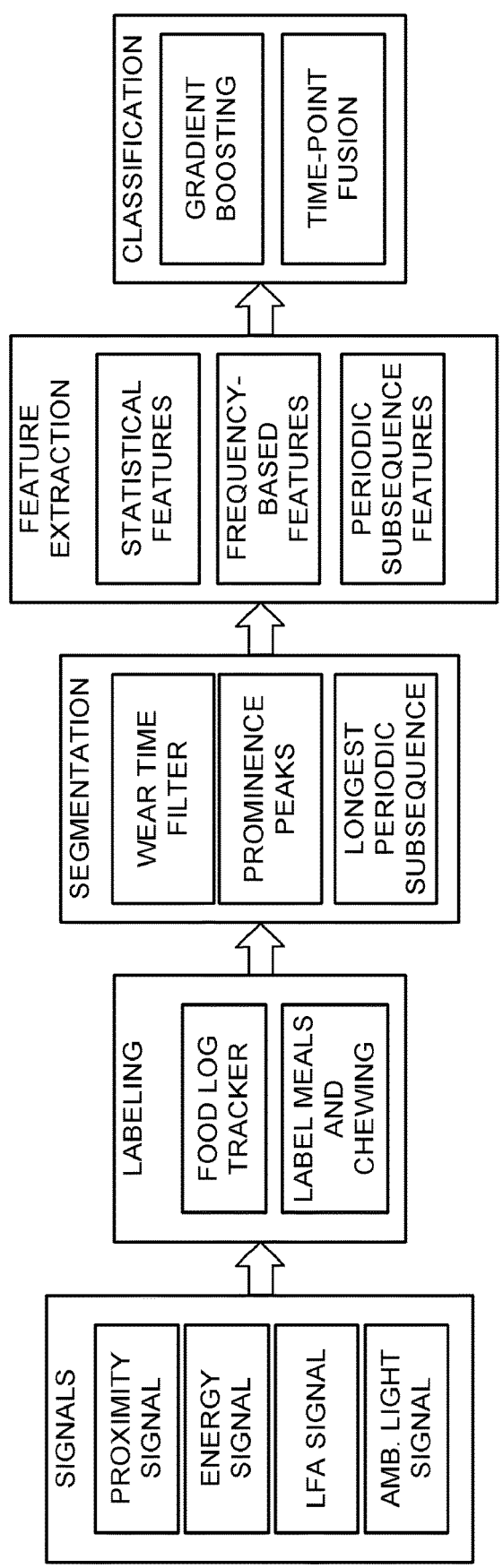
FIG. 20 illustrates example systems and methods described herein applied to a chewing and eating detection framework.

FIG. 20 illustrates the systems and methods described above applied to a chewing and eating detection framework 2000. As shown in the example of FIG. 20, one or more signals such as a proximity signal, energy signal, ambient light signal, and lean forward angle (LFA) signal are acquired from the example device 1300. The LFA can be calculated by applying a dot product of the normal vectors of two planes to define the LFA as the angle between the IMU and Earth's surface:

$$LFA = a\cos\langle n1, n2\rangle \quad \text{(Eq. 4)},$$

where the normal vector of the Earth's surface is the z-axis and the normal vector of the IMU is obtained through quaternion transformation:

$$n1=[0,0,1] \quad n2=qn1q^{-1} \quad \text{(Eq. 5)},$$

where q is a unit quaternion that rotates n1 to obtain the normal vector of the IMU. The IMU can also provide a triaxial accelerometer (ax, ay, az) capturing acceleration from three axes to calculate an energy sum as the sum of squares of the accelerometer:

$$E = a_x^2 + a_y^2 + a_z^2 \quad \text{(Eq. 6)}.$$

Chewing and/or other environmental context trigger can be used to trigger image data capture and/or correlate captured image data to determined user events (e.g., chewing, swallowing, breathing, etc.). Errors can be determined (e.g., based on time stamp, period, etc.) as well to help ensure an erroneous trigger does not result in capture of erroneous/inapplicable data. Features can be extracted including maximum, minimum, mean, median, variance, root mean square (RMS), correlation, skew, kurtosis, first and third interquartile range, interquartile range, etc. Extracted features can be gradient boosted and/or otherwise processed to select certain features, clean up feature data, etc., for analysis. In certain examples, features can be gathered, analyzed, fused, etc., over time.

As shown in the example of FIG. 20, captured signal information can be labeled to identify meals and chewing, track a food log, etc. Information can then be segmented based on a wear time filter for the device 1300, analysis of prominent peaks in acquired signal information, examination of period, etc. Features are extracted from the segmented information to identify statistical features, frequency-based features, periodic subsequence features, etc. Then features can be classified such as using gradient boosting, time-point fusion, etc., to better prepare the features for classification and application to food content and consumption analysis.

Thus, certain examples provide hyperspectral imaging analysis to distinguish foods and identify different levels of macromolecule content in those foods. To detect different food types, features can be generated from a variety of spectra (e.g., visible spectrum, near infrared spectrum, etc.), and improved accuracy can be achieved. Further, different levels of macromolecules can be detected using PCA to reduce dimensionality and employing an SVM classifier with an RBF kernel. The PCA plus SVM process can be applied to the entire spectrum rather than only RGB channels. Using a larger range of wavelengths is useful in more accurately determining the nutritional content in a food, especially when two samples look the same but are different in their macromolecule contents. In addition, in some instances, fusing the results of hyperspectral and RGB classifiers can result in the greatest predictive power. This supports the notion that current databases of food images should be expanded to include hyperspectral images in order to increase the efficiency of automated image-based calorie detection. In certain examples, rather than or in addition to classifying macromolecule content, a regression model can be implemented to predict an amount of macromolecule present in samples. Thus, hyperspectral technology can be used to estimate the nutritional content of foods.

Certain examples provide systems, apparatus, methods, and computer readable storage media for hyperspectral analysis and item composition evaluation to classify a target.

An example hyperspectral imaging sensor system to identify item composition includes an imager to capture hyperspectral imaging data of one or more items with respect to a target. The example includes a sensor to be positioned with respect to the target to trigger capture of the image data by the imager based on a characteristic of the target. The example includes a processor to prepare the captured imaging data for analysis to at least: identify the one or more items; determine composition of the one or more items; calculate an energy intake associated with the one or more items; and classify the target based on the energy intake.

In certain examples, the one or more items include food items. In certain examples, the characteristic of the target includes at least one of chewing or swallowing. In certain examples, the sensor includes at least one of a proximity sensor, an inertial measurement unit, or a light sensor. In certain examples, the imager is to capture both hyperspectral imaging data and red-green-blue imaging data to be fused into combined imaging data for analysis. In certain examples, the energy intake is based on caloric content of the one or more items to be determined by analyzing the spectrum associated with the hyperspectral imaging data. In certain examples, the target is a person, and wherein the target is to be classified as overeating or undereating. In certain examples, to classify the target is based on a comparison of the energy intake to a calculation of energy expenditure for the target. In certain examples, analysis of the capture image data is to include a principal component analysis with a support vector machine including a radial basis function kernel.

An example hyperspectral imaging data processor includes an image calibrator to receive hyperspectral imaging data of one or more food items captured with respect to a target in response to a trigger by a sensor positioned with respect to the target; a food identifier to identify one or more food items in the hyperspectral imaging data to provide one or more identifications; a food quantifier to quantify the one or more food items in the hyperspectral imaging data to provide one or more quantities; an energy intake calculator to process the one or more identifications and the one or more quantities to calculate an energy intake associated with the one or more food items; and a data processor classify the target based on the energy intake.

At least one example non-transitory computer readable storage medium includes instructions which, when executed, cause at least one processor to at least: facilitate capture of hyperspectral imaging data representing one or more items with respect to a target, the capture based on a trigger from a sensor positioned with respect to the target; identify the one or more items; determine composition of the one or more items; calculate an energy intake associated with the one or more items; and classify the target based on the energy intake.

An example method of hyperspectral imaging to identify item composition includes facilitating acquisition of hyperspectral imaging data representing one or more items with respect to a target, the capture based on a trigger from a sensor positioned with respect to the target; identifying the one or more items; determining composition of the one or more items; calculating an energy intake associated with the one or more items; and classifying the target based on the energy intake.

An example hyperspectral image analyzer apparatus includes: means for facilitating acquisition of hyperspectral imaging data representing one or more items with respect to a target, the capture based on a trigger from a sensor positioned with respect to the target; means for identifying the one or more items; means for determining composition of the one or more items; means for calculating an energy intake associated with the one or more items; and means for classifying the target based on the energy intake. The example apparatus can further include means for calculating energy expenditure of the target for comparison to the energy intake to classify the target based on the energy intake and energy expenditure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A hyperspectral imaging sensor system to identify item composition, the system comprising:
   an imager to capture hyperspectral imaging data of one or more items with respect to a human target;
   a sensor to be positioned with respect to the human target to trigger capture of the image data by the imager based on a characteristic of the human target; and
   a processor to prepare the captured imaging data for analysis to at least:
   identify the one or more items;
   determine composition of the one or more items;
   calculate an energy intake associated with the one or more items; and
   classify a status of the human target based on the energy intake.

2. The system of claim 1, wherein the one or more items include food items.

3. The system of claim 1, wherein the characteristic of the human target includes at least one of chewing or swallowing.

4. The system of claim 1, wherein the sensor includes at least one of a proximity sensor, an inertial measurement unit, or a light sensor.

5. The system of claim 1, wherein the imager is to capture both hyperspectral imaging data and red-green-blue imaging data to be fused into combined imaging data for analysis.

6. The system of claim 1, wherein the energy intake is based on caloric content of the one or more items to be determined by analyzing the spectrum associated with the hyperspectral imaging data.

7. The system of claim 1, wherein classification of the status of the human target is based on a comparison of the energy intake to a calculation of energy expenditure for the human target.

8. The system of claim 1, wherein analysis of the capture image data is to include a principal component analysis with a support vector machine including a radial basis function kernel.

9. At least one non-transitory computer readable storage medium including instructions which, when executed, cause at least one processor to at least:
   facilitate capture of hyperspectral imaging data representing one or more items with respect to a human target, the capture based on a trigger from a sensor positioned with respect to the human target;
   identify the one or more items;
   determine composition of the one or more items;

calculate an energy intake associated with the one or more items; and classify a status of the human target based on the energy intake.

10. The at least one non-transitory computer readable storage medium of claim 9, wherein the characteristic of the human target includes at least one of chewing or swallowing.

11. The at least one non-transitory computer readable storage medium of claim 9, wherein the sensor includes at least one of a proximity sensor, an inertial measurement unit, or a light sensor.

12. The at least one non-transitory computer readable storage medium of claim 9, wherein the imager is to capture both hyperspectral imaging data and red-green-blue imaging data to be fused into combined imaging data for analysis.

13. The at least one non-transitory computer readable storage medium of claim 9, wherein the energy intake is based on caloric content of the one or more items to be determined by analyzing the spectrum associated with the hyperspectral imaging data.

14. The at least one non-transitory computer readable storage medium of claim 9, wherein the human target is to be classified as overeating or undereating.

15. The at least one non-transitory computer readable storage medium of claim 9, wherein classification of the status of the human target is based on a comparison of the energy intake to a calculation of energy expenditure for the human target.

16. The at least one non-transitory computer readable storage medium of claim 9, wherein analysis of the capture image data is to include a principal component analysis with a support vector machine including a radial basis function kernel.

17. A method of hyperspectral imaging to identify item composition, the method comprising:

facilitating acquisition of hyperspectral imaging data representing one or more items with respect to a human target, the capture based on a trigger from a sensor positioned with respect to the human target;

identifying the one or more items;

determining composition of the one or more items;

calculating an energy intake associated with the one or more items; and classifying a status of the human target based on the energy intake.

18. The method of claim 17, wherein the imager is to capture both hyperspectral imaging data and red-green-blue imaging data to be fused into combined imaging data for analysis.

19. The method of claim 17, wherein the energy intake is based on caloric content of the one or more items to be determined by analyzing the spectrum associated with the hyperspectral imaging data.

20. The method of claim 17, wherein analysis of the capture image data is to include a principal component analysis with a support vector machine including a radial basis function kernel.

* * * * *